United States Patent
Liu et al.

(10) Patent No.: US 7,429,594 B2
(45) Date of Patent: Sep. 30, 2008

(54) SUBSTITUTED HETEROCYCLIC COMPOUNDS AND METHODS OF USE

(75) Inventors: Longbin Liu, Thousand Oaks, CA (US); Patricia Lopez, West Hills, CA (US); Manoj Bajpai, Simi Valley, CA (US); Aaron C. Siegmund, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 467 days.

(21) Appl. No.: 10/923,067

(22) Filed: Aug. 20, 2004

(65) Prior Publication Data

US 2005/0043301 A1 Feb. 24, 2005

Related U.S. Application Data

(60) Provisional application No. 60/496,871, filed on Aug. 20, 2003.

(51) Int. Cl.
C07D 401/04 (2006.01)
A61K 31/519 (2006.01)
(52) U.S. Cl. .................... 514/259.1; 514/272; 544/279; 544/321
(58) Field of Classification Search ............. 544/279, 544/321; 514/259.1, 272
See application file for complete search history.

(56) References Cited

U.S. PATENT DOCUMENTS 6,096,753 A 8/2000 Spohr et al.

FOREIGN PATENT DOCUMENTS

| WO | WO 98/24780 | 6/1998 |
| WO | WO 98/24782 | 6/1998 |
| WO | WO 03/099808 | 12/2003 |

OTHER PUBLICATIONS

Douglas, Jr., Introduction to Viral Diseases, Cecil Textbook of Medicine, 20th Edition, vol. 2, pp. 1739-1747, 1996.*
Damasio, Alzheimer's Disease and Related Dementias, Cecil Textbook of Medicine, 20th Edition, vol. 2, pp. 1992-1996, 1996.*
Gamaraschi et al., High-density lipoproteins attenuate interleukin-6 production in endothelial cells exposed to pro-inflammatory stimuli, Biochimica et Biophysica Acta, 1736 (2005) pp. 136-143.*
Casanova et al., PubMed Abstract (Rev Neurol. 28(9):909-15) May 1999.*
Ben-Hur et al., Cytokine-mediated modulation of MMPs and TIMPs in multipotential neural precursor cells, Journal of Neuroimmunology 175 (2006) pp. 12-18.*
Vuolteenaho et al., Effects of TNFalpha-antagonists on nitric oxide production in human cartilage, Osteoarthritis and Cartilage (2002) 10, pp. 327-332.*
Meng, Inflammation in Atherosclerosis: New Opportunities for Drug Discover, Min-Reviews in Medicinal Chemistry, 2005, 5, pp. 33-40.*

* cited by examiner

Primary Examiner—Deepak Rao
(74) Attorney, Agent, or Firm—G. Prabhakar Reddy

(57) ABSTRACT

The present invention relates to compounds having the general formula

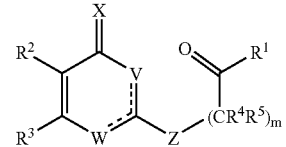

or a pharmaceutically acceptable salt thereof, wherein $R^1$ is a saturated or unsaturated 5-, 6- or 7-membered, ring containing 0, 1, 2 or 3 atoms selected from N, O and S, wherein the ring may be fused with a benzo group, and is substituted by 0, 1 or 2 oxo groups, and wherein $R^1$ is additionally substituted; and $R^2$ is a substituted $C_{1-6}$alkyl. Also included is a method of prophylaxis or treatment of inflammation, rheumatoid arthritis, Pagets disease, osteoporosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount a compound as described above.

15 Claims, No Drawings

SUBSTITUTED HETEROCYCLIC COMPOUNDS AND METHODS OF USE

This application claims the benefit of U.S. Provisional Application No. 60/496,871, filed Aug. 20, 2003, which is hereby incorporated by reference.

BACKGROUND OF THE INVENTION

The present invention comprises a new class of compounds useful in treating diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. This invention also relates to intermediates and processes useful in the preparation of such compounds.

Interleukin-1 (IL-1) and Tumor Necrosis Factor α (TNF-α) are pro-inflammatory cytokines secreted by a variety of cells, including monocytes and macrophages, in response to many inflammatory stimuli (e.g., lipopolysaccharide-LPS) or external cellular stress (e.g., osmotic shock and peroxide).

Elevated levels of TNF-α and/or IL-1 over basal levels have been implicated in mediating or exacerbating a number of disease states including rheumatoid arthritis; Pagets disease; osteoporosis; multiple myeloma; uveitis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It has been reported that TNF-α plays a role in head trauma, stroke, and ischemia. For instance, in animal models of head trauma (rat), TNF-α levels increased in the contused hemisphere (Shohami et al., *J. Cereb. Blood Flow Metab.* 14, 615 (1994)). In a rat model of ischemia wherein the middle cerebral artery was occluded, the levels of TNF-α mRNA of TNF-α increased (Feurstein et al., *Neurosci. Lett.* 164, 125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, *Stroke* 25, 1481 (1994)). TNF-α has also been implicated to play a role in type II diabetes (Endocrinol. 130, 43-52, 1994; and Endocrinol. 136, 1474-1481, 1995).

TNF-α appears to play a role in promoting certain viral life cycles and disease states associated with them. For instance, TNF-α secreted by monocytes induced elevated levels of HIV expression in a chronically infected T cell clone (Clouse et al., *J. Immunol.* 142, 431 (1989)). Lahdevirta et al., (*Am. J. Med.* 85, 289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8.

Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., *Clinical Immunol Immunopathol.* 55, 382 (1990)). In studies using cultured rheumatoid synovial cells, IL-1 is a more potent inducer of stromelysin than is TNF-α (Firestein, *Am. J. Pathol.* 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, *Eur. Cytokine Netw.* 5, 517-531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., *J. Immunol.* 136, 40 (1986)). Beutler et al. (*J. Immunol.* 135, 3969 (1985)) discussed the role of IL-1 in cachexia. Baracos et al. (*New Eng. J. Med.* 308, 553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., *Lymphokine Cytokine Res.* 11, 253 (1992); and Cooper, *Clin. Exp. Immunol.* 898, 244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195-223 (1995)). These approaches block the effects of TNF-α and IL-1 by either protein sequestration or receptor antagonism.

U.S. Pat. No. 5,100,897, incorporated herein by reference in its entirety, describes pyrimidinone compounds useful as angiotensin II antagonists wherein one of the pyrimidinone ring nitrogen atoms is substituted with a substituted phenylmethyl or phenethyl radical.

U.S. Pat. No. 5,162,325, incorporated herein by reference in its entirety, describes pyrimidinone compounds useful as angiotensin II antagonists wherein one of the pyrimidinone ring nitrogen atoms is substituted with a substituted phenylmethyl radical.

EP 481448, incorporated herein by reference in its entirety, describes pyrimidinone compounds useful as angiotensin II antagonists wherein one of the pyrimidinone ring nitrogen atoms is substituted with a substituted phenyl, phenylmethyl or phenethyl radical.

CA 2,020,370, incorporated herein by reference in its entirety, describes pyrimidinone compounds useful as angiotensin II antagonists wherein one of the pyrimidinone ring nitrogen atoms is substituted with a substituted biphenylaliphatic hydrocarbon radical.

BRIEF DESCRIPTION OF THE INVENTION

The present invention comprises a new class of compounds useful in the prophylaxis and treatment of diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. Accordingly, the invention also comprises pharmaceutical compositions comprising the compounds, methods for the prophylaxis and treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds of the invention are represented by the following general structure:

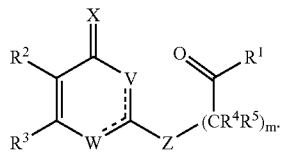

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with the present invention, there is provided compounds of the formula:

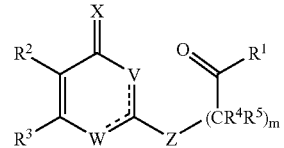

or a pharmacutically acceptable salt thereof, wherein

V is —N($R^7$)— or —N($R^{16}$)— and W is —C($R^6$)=; or V is —N($R^8$)— or —N($R^{16}$)— and W is —N=; or V is —N= and W is —N($R^8$)—;

X is O, S or $NR^9$;

Z is independently in each instance —O—, —N($R^9$)—, —N($R^{15}$)— —S(=O)$_n$—, —C(=O)O—, —OC(=O)—, —C(=O)N($R^9$)—, —N($R^9$)C(=O)—, —S(=O)$_2$N($R^9$)—, —N($R^9$)S(=O)$_2$—, —C(=N$R^9$)N($R^9$)—, —OC(=O)N($R^9$)—, —N($R^9$)C(=O)O—, —N($R^9$)C(=O)N($R^9$)— or —N($R^9$)C(=N$R^9$)N($R^9$)—;

m is 1, 2, 3, 4, 5 or 6;

n is independently in each instance 0, 1 or 2;

o is independently in each instance 0, 1, 2, 3 or 4;

$R^1$ is independently at each instance $C_{1-8}$alkyl substituted by 0 or 1 groups selected from $R^b$, —O($CH_2$)$_o$$R^b$, —N($R^a$)($CH_2$)$_o$$R^b$ and —S(=O)$_n$($CH_2$)$_o$$R^b$; and additionally substituted by 0, 1, 2 or 3 groups selected from —O$R^a$, —N($R^a$)$R^a$, —S(=O)$_n$($C_{1-6}$alkyl), —C(=O)O$R^a$, —OC(=O)($C_{1-6}$alkyl), —C(=O)N($R^a$)$R^a$, —N($R^9$)C(=O)($C_{1-6}$alkyl), —S(=O)$_2$N($R^a$)$R^a$, —N($R^a$)S(=O)$_2$($C_{1-6}$alkyl), —C(=N$R^a$)N($R^a$)$R^a$, —OC(=O)N($R^a$)$R^a$, —N($R^a$)C(=O)O$R^a$, —N($R^a$)C(=O)N($R^a$)$R^a$, —N($R^a$)C(=N$R^a$)N($R^a$)$R^a$, —OC(=O)N($R^a$)S(=O)$_2$($C_{1-6}$alkyl), —S(=O)$_2$N($R^a$)C(=O)($C_{1-6}$alkyl), —S(=O)$_2$N($R^a$)C(=O)O$R^a$, —S(=O)$_2$N($R^a$)C(=O)N($R^a$)$R^a$, —N($R^a$)S(=O)$_2$N($R^a$)$R^a$, oxo, cyano and halo;

$R^2$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of $R^{11}$, halo, cyano, —C(=O)$R^{11}$, —C(=O)O$R^{10}$, —C(=O)N$R^{12}$$R^{13}$, —C(N$R^{12}$)N$R^{12}$$R^{13}$, —O$R^{10}$, —O—C(=O)$R^{10}$, —O—C(=O)N$R^{12}$$R^{13}$, —O—C(=O)N$R^{14}$—S(=O)$_2$—$R^{11}$, —S$R^{10}$, —S(=O)$R^{11}$, —S(=O)$_2$—$R^{11}$, —S(=O)$_2$—N$R^{12}$$R^{13}$, —S(=O)$_2$—N$R^{14}$—C(=O)$R^{11}$, —S(=O)$_2$—N$R^{14}$—C(=O)O$R^{11}$, —S(=O)$_2$—N$R^{14}$—C(=O)N$R^{12}$$R^{13}$, —N$R^{12}$$R^{13}$, —N$R^{14}$—C(=O)$R^{10}$, —N$R^{14}$—C(=O)O$R^{11}$, —N$R^{14}$—C(=O)N$R^{12}$$R^{13}$, —N$R^{14}$—C(N$R^{12}$)N$R^{12}$$R^{13}$, —N$R^{14}$—S(=O)$_2$—$R^{11}$ or —N$R^{14}$S(=O)$_2$—N$R^{12}$$R^{13}$;

$R^3$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of $R^{11}$, halo, cyano, —C(=O)$R^{11}$, —C(=O)O$R^{10}$, —C(=O)N$R^{12}$$R^{13}$, —C(N$R^{12}$)N$R^{12}$$R^{13}$, —O$R^{10}$, —O—C(=O)$R^{10}$, —O—C(=O)N$R^{12}$$R^{13}$, —O—C(=O)N$R^{14}$—S(=O)$_2$—$R^{11}$, —S$R^{10}$, —S(=O)$R^{11}$, —S(=O)$_2$—$R^{11}$, —S(=O)$_2$—

$NR^{12}R^{13}$, $-S(=O)_2-NR^{14}-C(=O)R^{11}$, $-S(=O)_2-NR^{14}-C(=O)OR^{11}$, $-S(=O)_2-NR^{14}-C(=O)NR^{12}R^{13}$, $-NR^{12}R^{13}$, $-NR^{14}-C(=O)R^{10}$, $-NR^{14}-C(=O)OR^{11}$, $-NR^{14}-C(=O)NR^{12}R^{13}$, $-NR^{14}-C(NR^{12})NR^{12}R^{13}$, $-NR^{14}-S(=O)_2-R^{11}$ or $-NR^{14}-S(=O)_2-NR^{12}R^{13}$;

provided that the total number of aryl, heteroaryl, cycloalkyl and heterocyclyl radicals substituted on each of $R^2$ and $R^3$ is 0 or 1;

$R^4$ and $R^5$ are each independently in each instance $-OR^a$, $-N(R^a)R^a$, $-S(=O)_n(C_{1-6}alkyl)$, $-C(=O)OR^a$, $-OC(=O)(C_{1-6}alkyl)$, $-C(=O)N(R^a)R^a$, $-N(R^a)C(=O)(C_{1-6}alkyl)$, $-S(=O)_2N(R^a)R^a$, $-N(R^a)S(=O)_2(C_{1-6}alkyl)$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}alkyl)$, $-S(=O)_2N(R^a)C(=O)(C_{1-6}alkyl)$, $-S(=O)_2N(R^a)C(=O)OR^a$, $-S(=O)_2N(R^a)C(=O)N(R^a)R^a$, $-N(R^a)S(=O)_2N(R^a)R^a$, halo or cyano;

$R^6$ is independently in each instance hydrogen, $-R^1$ or $-Z-R^1$;

$R^7$ is independently in each instance hydrogen or $-R^1$;

$R^8$ is independently in each instance hydrogen or $-R^1$; provided that the total number of aryl, heteroaryl, cycloalkyl and heterocyclyl radicals in each $-R^1$ and $-Z-R^1$ is 0, 1, 2 or 3;

$R^9$ is independently at each instance hydrogen, $R^b$ or $C_{1-8}$alkyl substituted by 0 or 1 groups selected from $R^b$, $-O(CH_2)_oR^b$, $-N(R^a)(CH_2)_oR^b$ and $-S(=O)_n(CH_2)_oR^b$; and additionally substituted by 0, 1, 2 or 3 groups selected from $-OR^a$, $-N(R^a)R^a$, $-S(=O)_n(C_{1-6}alkyl)$, $-C(=O)OR^a$, $-OC(=O)(C_{1-6}alkyl)$, $-C(=O)N(R^a)R^a$, $-N(R^9)C(=O)(C_{1-6}alkyl)$, $-S(=O)_2N(R^a)R^a$, $-N(R^a)S(=O)_2(C_{1-6}alkyl)$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}alkyl)$, $-S(=O)_2N(R^a)C(=O)(C_{1-6}alkyl)$, $-S(=O)_2N(R^a)C(=O)OR^a$, $-S(=O)_2N(R^a)C(=O)N(R^a)R^a$, $-N(R^a)S(=O)_2N(R^a)R^a$, oxo, cyano and halo;

$R^{10}$ is independently at each instance hydrogen or $R^{11}$;

$R^{11}$ is independently at each instance $C_{1-8}$alkyl substituted by 0 or 1 groups selected from $R^b$, $-O(CH_2)_oR^b$, $-N(R^a)(CH_2)_oR^b$ and $-S(=O)_n(CH_2)_oR^b$; and additionally substituted by 0, 1, 2 or 3 groups selected from $-OR^a$, $-N(R^a)R^a$, $-S(=O)_n(C_{1-6}alkyl)$, $-C(=O)OR^a$, $-OC(=O)(C_{1-6}alkyl)$, $-C(=O)N(R^a)R^a$, $-N(R^9)C(=O)(C_{1-6}alkyl)$, $-S(=O)_2N(R^a)R^a$, $-N(R^a)S(=O)_2(C_{1-6}alkyl)$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}alkyl)$, $-S(=O)_2N(R^a)C(=O)(C_{1-6}alkyl)$, $-S(=O)_2N(R^a)C(=O)OR^a$, $-S(=O)_2N(R^a)C(=O)N(R^a)R^a$, $-N(R^a)S(=O)_2N(R^a)R^a$, oxo, cyano and halo;

$R^{12}$ is independently at each instance hydrogen, $R^b$ or $C_{1-8}$alkyl substituted by 0 or 1 groups selected from $R^b$, $-O(CH_2)_oR^b$, $-N(R^a)(CH_2)_oR^b$ and $-S(=O)_n(CH_2)_oR^b$; and additionally substituted by 0, 1, 2 or 3 groups selected from $-OR^a$, $-N(R^a)R^a$, $-S(=O)_n(C_{1-6}alkyl)$, $-C(=O)OR^a$, $-OC(=O)(C_{1-6}alkyl)$, $-C(=O)N(R^a)R^a$, $-N(R^9)C(=O)(C_{1-6}alkyl)$, $-S(=O)_2N(R^a)R^a$, $-N(R^a)S(=O)_2(C_{1-6}alkyl)$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}alkyl)$, $-S(=O)_2N(R^a)C(=O)(C_{1-6}alkyl)$, $-S(=O)_2N(R^a)C(=O)OR^a$, $-S(=O)_2N(R^a)C(=O)N(R^a)R^a$, $-N(R^a)S(=O)_2N(R^a)R^a$, oxo, cyano and halo;

$R^{13}$ is independently at each instance: is independently at each instance hydrogen, $R^b$ or $C_{1-8}$alkyl substituted by 0 or 1 groups selected from $R^b$, $-O(CH_2)_oR^b$, $-N(R^a)(CH_2)_oR^b$ and $-S(=O)_n(CH_2)_oR^b$; and additionally substituted by 0, 1, 2 or 3 groups selected from $-OR^a$, $-N(R^a)R^a$, $-S(=O)_n(C_{1-6}alkyl)$, $-C(=O)OR^a$, $-OC(=O)(C_{1-6}alkyl)$, $-C(=O)N(R^a)R^a$, $-N(R^9)C(=O)(C_{1-6}alkyl)$, $-S(=O)_2N(R^a)R^a$, $-N(R^a)S(=O)_2(C_{1-6}alkyl)$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}alkyl)$, $-S(=O)_2N(R^a)C(=O)(C_{1-6}alkyl)$, $-S(=O)_2N(R^a)C(=O)OR^a$, $-S(=O)_2N(R^a)C(=O)N(R^a)R^a$, $-N(R^a)S(=O)_2N(R^a)R^a$, oxo, cyano and halo;

$R^{14}$ is independently at each instance hydrogen or $C_{1-8}$alkyl substituted by 0 or 1 groups selected from $R^b$, $-O(CH_2)_oR^b$, $-N(R^a)(CH_2)_oR^b$ and $-S(=O)_n(CH_2)_oR^b$; and additionally substituted by 0, 1, 2 or 3 groups selected from $-OR^a$, $-N(R^a)R^a$, $-S(=O)_n(C_{1-6}alkyl)$, $-C(=O)OR^a$, $-OC(=O)(C_{1-6}alkyl)$, $-C(=O)N(R^a)R^a$, $-N(R^9)C(=O)(C_{1-6}alkyl)$, $-S(=O)_2N(R^a)R^a$, $-N(R^a)S(=O)_2(C_{1-6}alkyl)$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}alkyl)$, $-S(=O)_2N(R^a)C(=O)(C_{1-6}alkyl)$, $-S(=O)_2N(R^a)C(=O)OR^a$, $-S(=O)_2N(R^a)C(=O)N(R^a)R^a$, $-N(R^a)S(=O)_2N(R^a)R^a$, oxo, cyano and halo;

$R^{15}$ and $R^{16}$ together represent a saturated or unsaturated 2-, 3- or 4-carbon bridge substituted by 0, 1, 2 or 3 substituents selected from $-OR^a$, $-N(R^a)R^a$, $-S(=O)_n(C_{1-6}alkyl)$, $-C(=O)OR^a$, $-OC(=O)(C_{1-6}alkyl)$, $-C(=O)N(R^a)R^a$, $-N(R^a)C(=O)(C_{1-6}alkyl)$, $-S(=O)_2N(R^a)R^a$, $-N(R^a)S(=O)_2(C_{1-6}alkyl)$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}alkyl)$, $-S(=O)_2N(R^a)C(=O)(C_{1-6}alkyl)$, $-S(=O)_2N(R^a)C(=O)OR^a$, $-S(=O)_2N(R^a)C(=O)N(R^a)R^a$, $-N(R^a)S(=O)_2N(R^a)R^a$, halo and cyano;

$R^a$ is independently in each instance hydrogen or $C_{1-6}$alkyl; and $R^b$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group; and wherein the phenyl, naphthyl or heterocycle is substituted with 0, 1, 2 or 3 substituents selected from $-OR^a$, $-N(R^a)R^a$, $-S(=O)_n(C_{1-6}alkyl)$, $-C(=O)OR^a$, $-OC(=O)(C_{1-6}alkyl)$, $-C(=O)N(R^a)R^a$, $-N(R^a)C(=O)(C_{1-6}alkyl)$, $-S(=O)_2N(R^a)R^a$, $-N(R^a)S(=O)_2(C_{1-6}alkyl)$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}alkyl)$, $-S(=O)_2N(R^a)C(=O)(C_{1-6}alkyl)$, $-S(=O)_2N(R^a)C(=O)OR^a$, $-S(=O)_2N(R^a)C(=O)N(R^a)R^a$, $-N(R^a)S(=O)_2N(R^a)R^a$, cyano, halo, $C_{1-4}$alkyl and $C_{1-4}$haloalkyl.

In another embodiment, in conjunction with any of the above or below embodiments, $R^3$ is a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of $R^{11}$, halo, cyano, $-C(=O)R^{11}$, $-C(=O)OR^{10}$, $-C(=O)NR^{12}R^{13}$, $-C(NR^{12})NR^{12}R^{13}$, $-OR^{10}$, $-O-C(=O)R^{10}$, $-O-C(=O)NR_{12}R_{13}$, $-O-C(=O)NR^{14}-S(=O)_2-R^{11}$, $-SR^{10}$, $-S(=O)R^{11}$, $-S(=O)_2-R^{11}$, $-S(=O)_2-$ $NR^{12}R^{13}$, $-S(=O)_2-NR^{14}-C(=O)R^{11}$, $-S(=O)_2-NR^{14}-C(=O)OR^{11}$, $-S(=O)_2-NR^{14}-C(=O)NR^{12}R^{13}$, $-NR^{12}R^{13}$, $-NR^{14}-C(=O)R^{10}$, $-NR^{14}-C(=O)OR^{11}$, $-NR^{14}-C(=O)NR^{12}R^{13}$, $-NR^{14}-C(NR^{12})NR^{12}R^{13}$, $-NR^{14}-S(=O)_2-R^{11}$ or $-NR^{14}-S(=O)_2-NR^{12}R^{13}$.

In another embodiment, in conjunction with any of the above or below embodiments, $R^3$ is pyridinyl or pyrimidinyl, either of which are substituted by 0, 1, 2 or 3 radicals of $R^{11}$, halo, cyano, $-C(=O)R^{11}$, $-C(=O)OR^{10}$, $-C(=O)NR^{12}R^{13}$, $-C(NR^{12})NR^{12}R^{13}$, $-OR^{10}$, $-O-C(=O)R^{10}$, $-O-C(=O)NR^{12}R^{13}$, $-O-C(=O)NR^{14}-S(=O)_2-R^{11}$, $-SR^{10}$, $-S(=O)R^{11}$, $-S(=O)_2-R^{11}$, $-S(=O)_2-NR^{12}R^{13}$, $-S(=O)_2-NR^{14}-C(=O)R^{11}$, $-S(=O)_2-NR^{14}-C(=O)OR^{11}$, $-S(=O)_2-NR^{14}-C(=O)NR^{12}R^{13}$, $-NR^{12}R^{13}$, $-NR^{14}-C(=O)R^{10}$, $-NR^{14}-C(=O)OR^{11}$, $-NR^{14}-C(=O)NR^{12}R^{13}$, $-NR^{14}-C(NR^{12})NR^{12}R^{13}$, $-NR^{14}-S(=O)_2-R^{11}$ or $-NR^{14}-S(=O)_2-NR^{12}R^{13}$.

In another embodiment, in conjunction with any of the above or below embodiments, $R^2$ is phenyl or naphthyl, either of which is substituted by 0, 1, 2 or 3 radicals of $R^{11}$, halo, cyano, $-C(=O)R^{11}$, $-C(=O)OR^{10}$, $-C(=O)NR^{12}R^{13}$, $-C(NR^{12})NR^{12}R^{13}$, $-OR^{10}$, $-O-C(=O)R^{10}$, $-O-C(=O)NR^{12}R^{13}$, $-O-C(=O)NR^{14}-S(=O)_2-R^{11}$, $-SR^{10}$, $-S(=O)R^{11}$, $-S(=O)_2-R^{11}$, $-S(=O)_2-NR^{12}R^{13}$, $-S(=O)_2-NR^{14}-C(=O)R^{11}$, $-S(=O)_2-NR^{14}-C(=O)OR^{11}$, $-S(=O)_2-NR^{14}-C(=O)NR^{12}R^{13}$, $-NR^{12}R^{13}$, $-NR^{14}-C(=O)R^{10}$, $-NR^{14}-C(=O)OR^{11}$, $-NR^{14}-C(=O)NR^{12}R^{13}$, $-NR^{14}-C(NR^{12})NR^{12}R^{13}$, $-NR^{14}-S(=O)_2-R^{11}$ or $-NR^{14}S(=O)_2-NR^{12}R^{13}$.

In another embodiment, in conjunction with any of the above or below embodiments, $R^1$ is $C_{1-8}$alkyl.

In another embodiment, in conjunction with any of the above or below embodiments, $R^1$ is independently at each instance $C_{1-8}$alkyl substituted by 0 or 1 groups selected from $R^b$, $-O(CH_2)_oR^b$, $-N(R^a)(CH_2)_oR^b$ and $-S(=O)_n(CH_2)_oR^b$; and additionally substituted by 1, 2 or 3 groups selected from $-OR^a$, $-N(R^a)R^a$, $-S(=O)_n(C_{1-6}\text{alkyl})$, $-C(=O)OR^a$, $-OC(=O)(C_{1-6}\text{alkyl})$, $-C(=O)N(R^a)R^a$, $-N(R^9)C(=O)(C_{1-6}\text{alkyl})$, $-S(=O)_2N(R^a)R^a$, $-N(R^a)S(=O)_2(C_{1-6}\text{alkyl})$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}\text{alkyl})$, $-S(=O)_2N(R^a)C(=O)(C_{1-6}\text{alkyl})$, $-S(=O)_2N(R^a)C(=O)OR^a$, $-S(=O)_2N(R^a)C(=O)N(R^a)R^a$, $-N(R^a)S(=O)_2N(R^a)R^a$, oxo, cyano and halo.

In another embodiment, in conjunction with any of the above or below embodiments, the group $(CR^4R^5)_m$ is $C_{1-6}$alkyl substituted by 1 or 2 substituents selected from $-OR^a$, $-N(R^a)R^a$, $-S(=O)_n(C_{1-6}\text{alkyl})$, $-C(=O)OR^a$, $-OC(=O)(C_{1-6}\text{alkyl})$, $-C(=O)N(R^a)R^a$, $-N(R^a)C(=O)(C_{1-6}\text{alkyl})$, $-S(=O)_2N(R^a)R^a$, $-N(R^a)S(=O)_2(C_{1-6}\text{alkyl})$, $-C(=NR^a)N(R^a)R^a$, $-OC(=O)N(R^a)R^a$, $-N(R^a)C(=O)OR^a$, $-N(R^a)C(=O)N(R^a)R^a$, $-N(R^a)C(=NR^a)N(R^a)R^a$, $-OC(=O)N(R^a)S(=O)_2(C_{1-6}\text{alkyl})$, $-S(=O)_2N(R^a)C(=O)(C_{1-6}\text{alkyl})$, $-S(=O)_2N(R^a)C(=O)OR^a$, $-S(=O)_2N(R^a)C(=O)N(R^a)R^a$, $-N(R^a)S(=O)_2N(R^a)R^a$, halo or cyano.

In another embodiment, in conjunction with any of the above or below embodiments, $R^4$ and $R^5$ are both H.

In another embodiment, in conjunction with any of the above or below embodiments, Z is $-N(R^9)-$, $-N(R^{15})-$, $-N(R^9)C(=O)-$, $-N(R^9)S(=O)_2-$, $-N(R^9)C(=O)O-$, $-N(R^9)C(=O)N(R^9)-$ or $-N(R^9)C(=NR^9)N(R^9)-$.

In another embodiment, in conjunction with any of the above or below embodiments, $R^2$ is not pyridyl, pyrimidinyl, quinolyl or isoquinolinyl.

In another embodiment, in conjunction with any of the above or below embodiments, V is $-N(R^7)-$ or $-N(R^{16})-$ and W is $-C(R^6)=$.

In another embodiment, in conjunction with any of the above or below embodiments, V is $-N(R^8)-$ or $-N(R^{16})-$ and W is $-N=$.

In another embodiment, in conjunction with any of the above or below embodiments, V is $-N=$ and W is $-N(R^8)-$.

Another aspect of the invention relates to a pharmaceutical composition comprising a compound according to any one of the above embodiments and a pharmaceutically acceptable carrier.

Another aspect of the invention relates to a method of prophylaxis or treatment of inflammation comprising administering an effective amount of a compound according to any one of the above embodiments.

Another aspect of the invention relates to a method of prophylaxis or treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount of a compound according to any one of the above embodiments.

Another aspect of the invention relates to a method of lowering plasma concentrations of either or both TNF-a and IL-1 comprising administering an effective amount of a compound according to any one of the above embodiments.

Another aspect of the invention relates to a method of lowering plasma concentrations of either or both IL-6 and IL-8 comprising administering an effective amount of a compound according to any one of the above embodiments.

Another aspect of the invention relates to a method of prophylaxis or treatment of diabetes disease in a mammal comprising administering an effective amount of a compound according to any one of the above embodiments to produce a glucagon antagonist effect.

Another aspect of the invention relates to a method of prophylaxis or treatment of a pain disorder in a mammal comprising administering an effective amount of a compound according to any one of the above embodiments.

Another aspect of the invention relates to a method of decreasing prostaglandins production in a mammal comprising administering an effective amount of a compound according to any one of the above embodiments.

Another aspect of the invention relates to a method of decreasing cyclooxygenase enzyme activity in a mammal comprising administering an effective amount of a compound according to any one of the above embodiments. In another embodiment, the cyclooxygenase enzyme is COX-2.

Another aspect of the invention relates to a method of decreasing cyclooxygenase enzyme activity in a mammal comprising administering an effective amount of the above pharmaceutical composition. In another embodiment the cyclooxygenase enzyme is COX-2.

Another aspect of the invention relates to the manufacture of a medicament comprising a compound according to any one of the above embodiments.

Another aspect of the invention relates to the manufacture of a medicament for the treatment of inflammation comprising administering an effective amount of a compound according to any one of the above embodiments.

Another aspect of the invention relates to the manufacture of a medicament for the treatment of rheumatoid arthritis, Pagets disease, osteoporosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount of a compound according to any one of the above embodiments.

The compounds of this invention may have in general several asymmetric centers and are typically depicted in the form of racemic mixtures. This invention is intended to encompass racemic mixtures, partially racemic mixtures and separate enantiomers and diasteromers.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Unless otherwise specified, the following definitions apply to terms found in the specification and claims:

"Aryl" means a phenyl or naphthyl radical, wherein the phenyl may be fused with a $C_{3-4}$cycloalkyl bridge.

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

"$C_{\alpha-\beta}$alkyl" means an alkyl group comprising from α to β carbon atoms in a branched, cyclical or linear relationship or any combination of the three. The alkyl groups described in this section may also contain double or triple bonds. Examples of $C_{1-8}$alkyl include, but are not limited to the following:

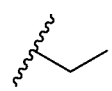 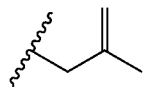 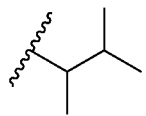

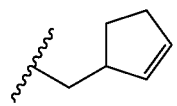

"Halogen" and "halo" mean a halogen atoms selected from F, Cl, Br and I.

"$C_{\alpha-\beta}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

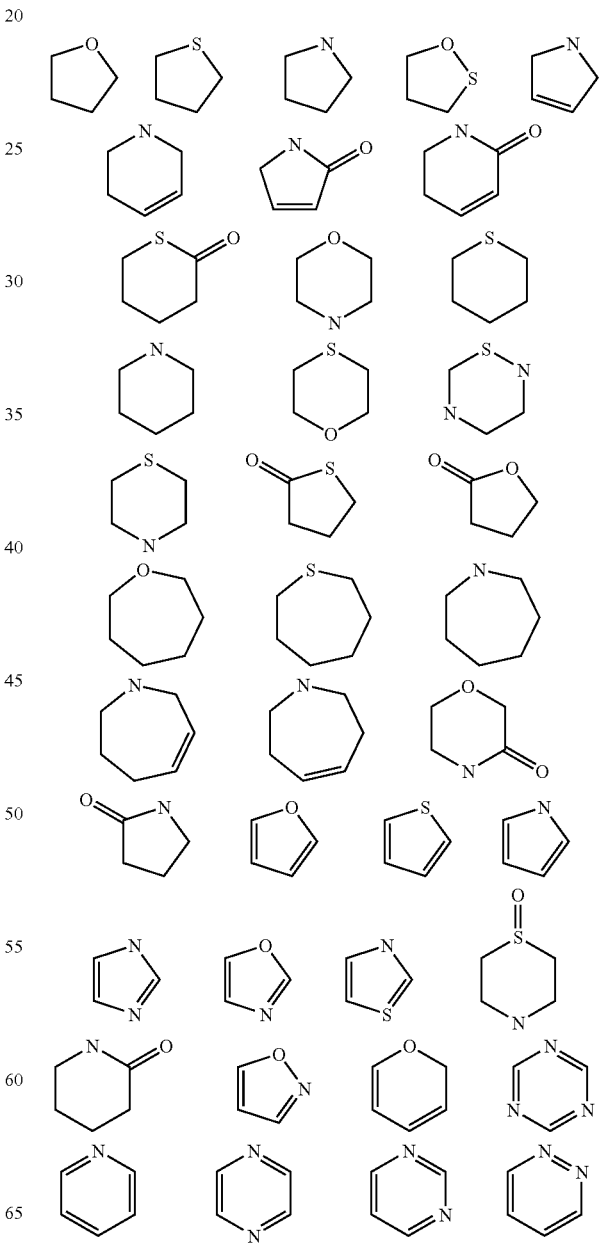

-continued

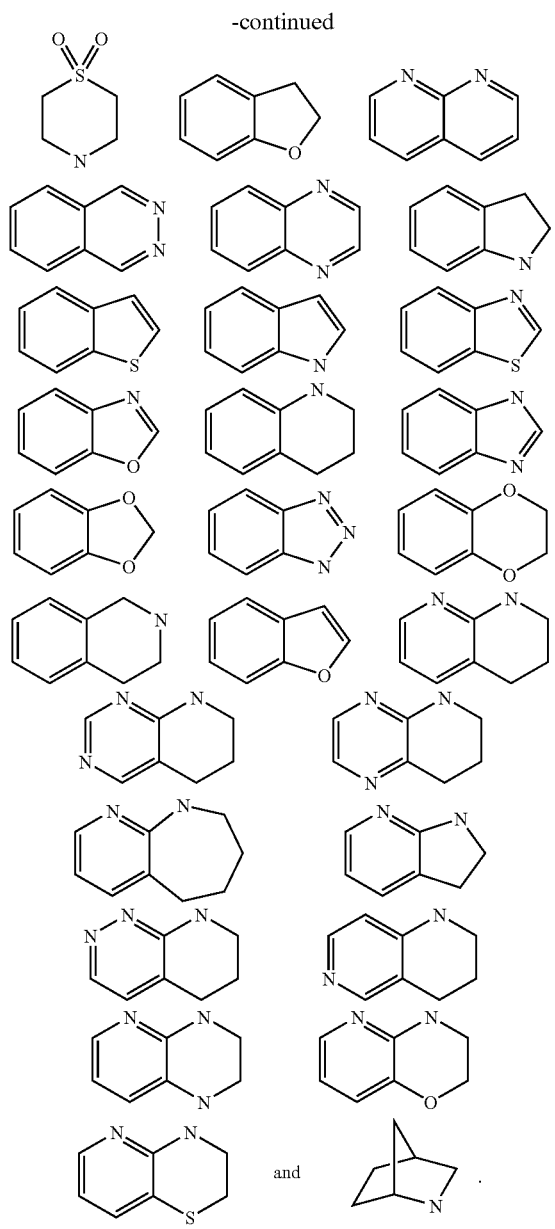

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

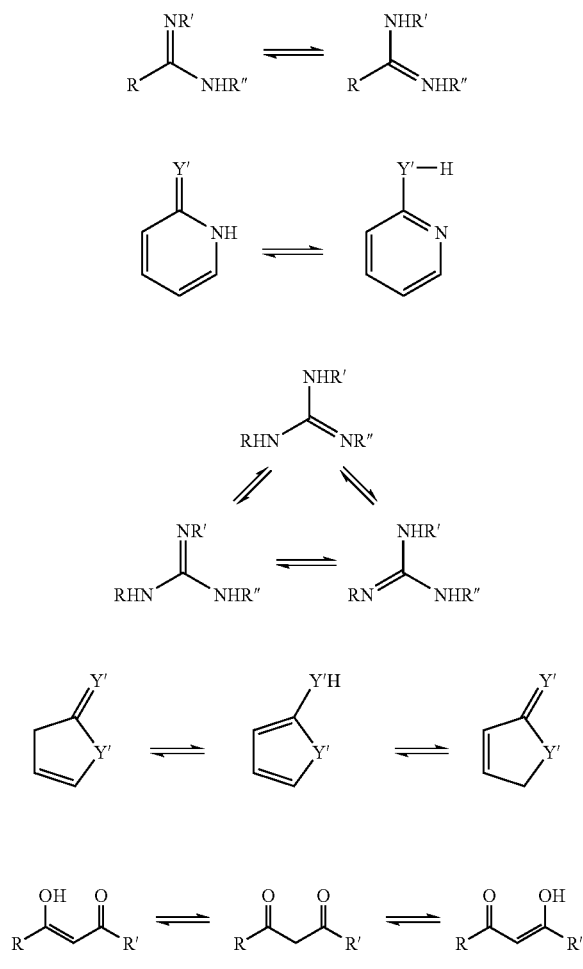

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

"Cytokine" means a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

"TNF, IL-1, IL-6, and/or IL-8 mediated disease or disease state" means all disease states wherein TNF, IL-1, IL-6, and/or IL-8 plays a role, either directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of or action of IL-1 is a result of TNF, would be considered mediated by TNF.

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

4(3H)-Pyrimidinones:

For the synthesis of 4(3H)-pyrimidinones II (or its tautomer, 4-hydroxy-pyrmidines), the approach displayed in Scheme 1 may be followed (for a review of synthetic methods see: D. J. Brown, Heterocyclic Compounds: the Pyrimidines, supra). This approach involves the cyclization reaction between an acrylic acid ester XII and an amidine V followed by oxidation of the resulting dihydropyrimidinone XIII to give II.

Scheme 1

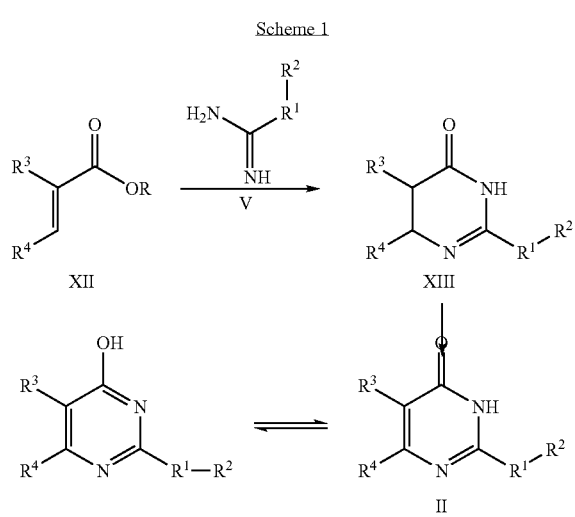

For the synthesis of 2-substituted 5-(4-fluorophenyl)-6-(4-pyridyl)-4-hydroxy-pyrimidines II (Scheme 2), the disubstituted acrylic acid ester XII may be prepared conveniently by condensation of pyridine-4-carboxaldehyde with 4-fluorophenylacetic acid followed by esterification. XII may be reacted with a variety of amidines V at elevated temperature. As a dehydrogenating agent for the conversion of XIII to II, sodium nitrite/acetic acid is suitable.

Accordingly, further compounds of formula II may be obtained in which $R^4$ is any other heteroaryl ring within the definition of $R^4$ by the appropriate choice of starting material. Such starting materials include but are not limited to 2-methylpyridine-4-carboxaldehyde, 2,6-dimethylpyridine-4-carboxaldehyde (Mathes and Sauermilch, Chem. Ber. 88, 1276-1283 (1955)), quinoline-4-carboxaldehyde, pyrimidine-4-carboxaldehyde, 6-methylpyrimidine-4-carbox-aldehyde, 2-methylpyrimidine-4-carboxaldehyde, 2,6-dimethylpyrimidine-4-carboxalde-hyde (Bredereck et al., Chem. Ber. 97, 3407-3417 (1964)). The use of 2-nitropyridine-4-carboxaldehyde would lead to a derivative of formula II with $R^4$ represented by a 2-nitro-4-pyridyl group. Catalytic reduction of the nitro to an amino group would provide the 2-amino-4-pyridyl derivative of II. The approach displayed in Scheme 2 is applicable to the use of other aryl acetic acids leading to compounds of formula II with different aryl groups as $R^3$.

Pyrimidinone II ($R^1$=H) may be substituted at the N-3 position by reaction with e.g. an alkyl halide, such as methyl iodide or ethyl bromide in the presence of an appropriate base such as potassium carbonate and the like.

Scheme 2

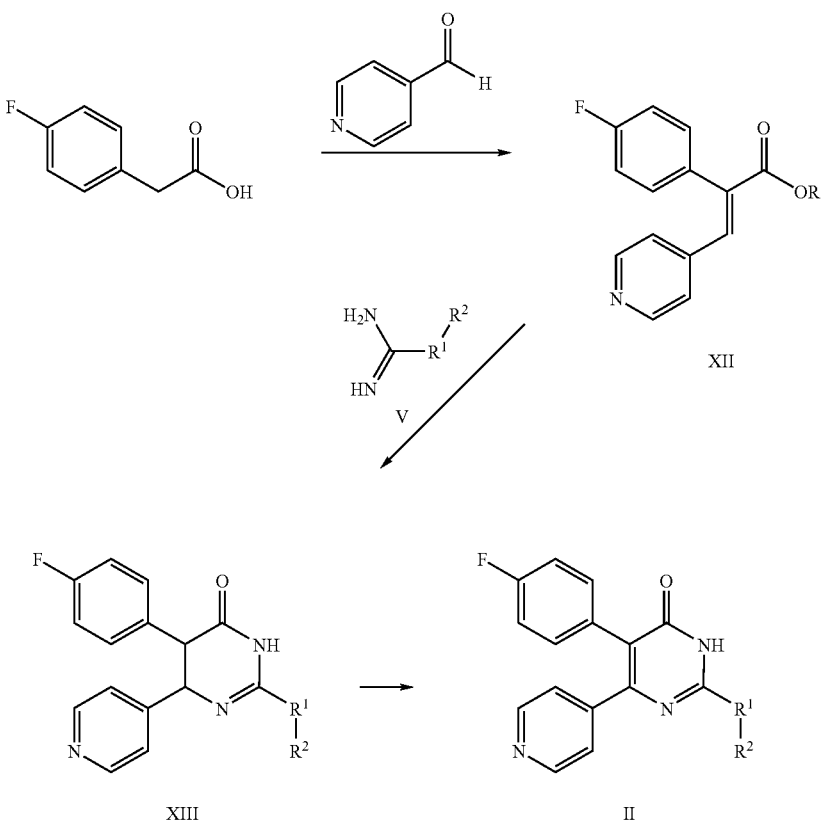

Scheme 3

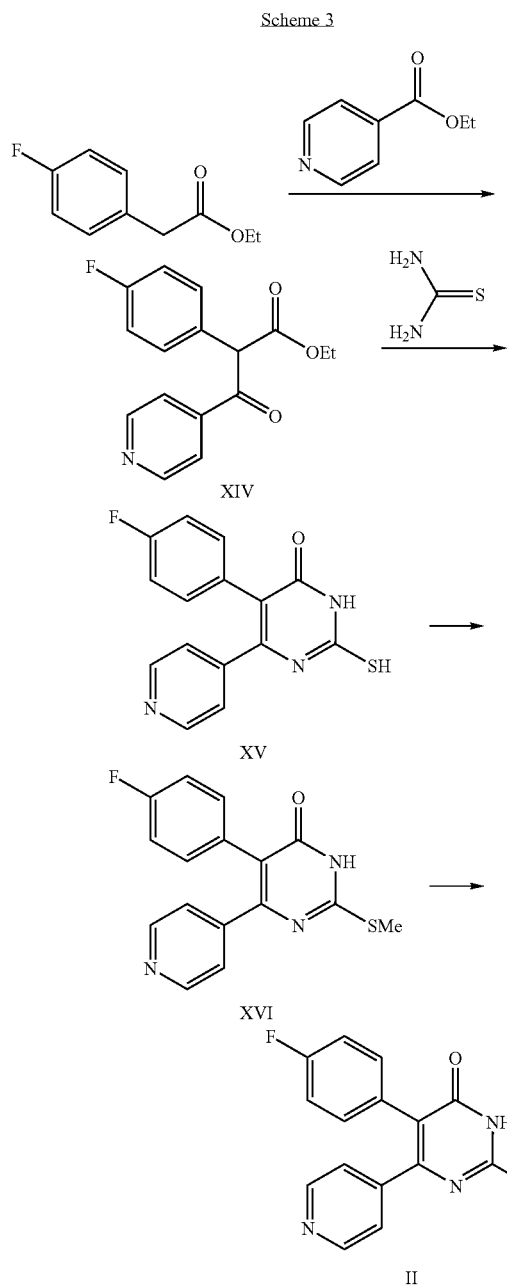

Another approach (Scheme 3) leading to 5,6-diaryl-4-hydroxy-pyrimidines involves the cyclization of the b-keto ester XIV with thiourea to give the thiouracil derivative XV. XV can be S-monomethylated to XVI. Reaction of XVI with primary and secondary amines gives 2-amino substituted 4-hydroxypyrimidines II.

Although Scheme 3 illustrates syntheses in which $R^4$ is 4-pyridyl, this approach may be equally applied to any other heteroaryl ring within the definition of $R^4$ by the appropriate choice of the starting material. Such starting materials include but are not limited to ethyl 2-methyl isonicotinate (Efimovsky and Rumpf, *Bull. Soc. Chim. FR.* 648-649 (1954)), methyl pyrimidine-4-carboxylate, methyl 2-methylpyrimidine-4-carboxylate, methyl 6-methylpyrimidine-4-carboxylate and methyl 2,6-dimethylpyrimidine-4-carboxylate (Sakasi et al., *Heterocycles* 13, 235 (1978)). Likewise, methyl 2-nitroisonicotinate (Stanonis, *J. Org. Chem.* 22, 475 (1957)) may be reacted with an aryl acetic acid ester followed by cyclization of the resultant β-keto ester with thiourea analogously to Scheme 3. Subsequent catalytic reduction of the nitro group to an amino group would give a pyrimidinone II in which $R^4$ is represented by a 2-amino-4-pyridyl group (Scheme 4).

Scheme 4

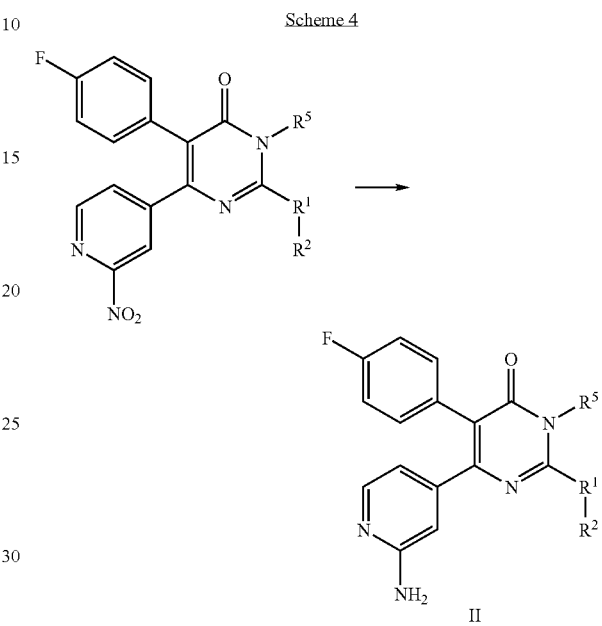

Furthermore, methyl 2-acetamido isonicotinate (Scheme 5) may be reacted analogously to Scheme 3 after appropriate protection of the amide nitrogen with e.g. a tert-butyldimethylsilyloxymethyl group (Benneche et al., *Acta Chem. Scand. B* 42 384-389 (1988)), a tert-butyldimethylsilyl group, a benzyloxymethyl group, a benzyl group or the like ($P_1$).

Scheme 5

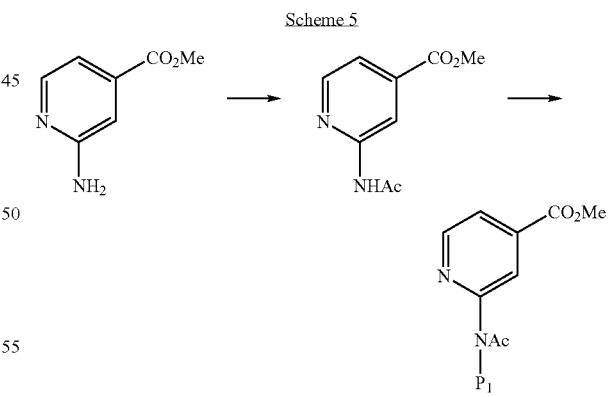

Removal of the protecting group $P_1$ of the resulting pyrimidine II with a suitable reagent (e.g., tetrabutylammonium fluoride in the case where $P_1$ is t-butyldimethyl-silyloxymethyl) would then lead to a pyrimidinone II with $R^4$ represented by a 2-acetamido-4-pyridyl group. Needless to say, ethyl p-fluorophenyl acetate may be substituted by any alkyl arylacetate in the procedure illustrated in Scheme 3 thus providing compounds of formula II with different $R^3$ aryl substituents.

In a further process, pyrimidinones II may be prepared by coupling a suitable derivative of XVIII (L is a leaving group, such as halogen radical and the like) with an appropriate aryl equivalent.

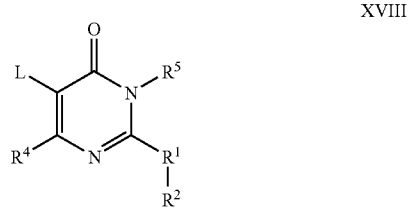

XVIII

Such aryl/heteroaryl couplings are well known to those skilled in the art and involve an organic-metallic component for reaction with a reactive derivative, e.g., a halogeno derivative, of the second compound in the presence of a catalyst. The metallo-organic species may be provided either by the pyrimidinone in which case the aryl component provides the reactive halogen equivalent or the pyrimidinone may be in the form of a reactive 5-halogeno derivative for reaction with a metallo organic aryl compound. Accordingly, 5-bromo and 5-iodo derivatives of XVIII (L=Br, I) may be treated with arylalkyl tin compounds, e.g., trimethylstannylbenzene, in an inert solvent such as tetrahydrofuran in the presence of a palladium catalyst, such as di(triphenylphosphine)palladium (II)dichloride. (Peters et al., *J. Heterocyclic Chem.* 27, 2165-2173, (1990). Alternatively, the halogen derivative of XVIII may be converted into a trialkyltin derivative (L=Bu$_3$Sn) by reaction with e.g. tributylstannyl chloride following lithiation with butyllithium and may then be reacted with an aryl halide in the presence of a catalyst. (Sandosham and Undheim, *Acta Chem. Scand.* 43, 684-689 (1989). Both approaches would lead to pyrimidines II in which R$^{11}$ is represented by aryl and heteroaryl groups.

As reported in the literature (Kabbe, *Lieb. Ann. Chem.* 704, 144 (1967); German Patent 1271116 (1968)) and displayed in Scheme 6, 5-aryl-2,6-dipyridyl-4(3H)-pyrimidinones II may be prepared in a one step synthesis by reaction of the cyanopyridine with an arylacetyl ester, such as ethyl phenylacetate in the presence of sodium methoxide.

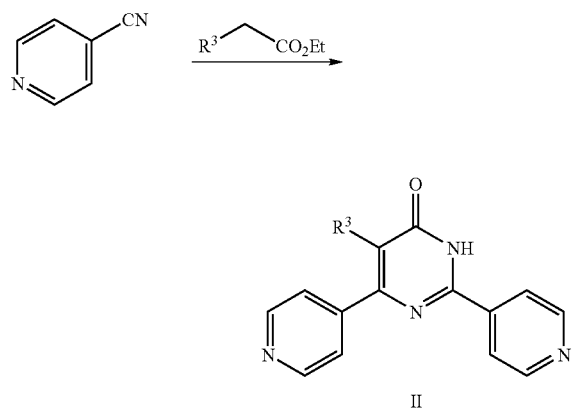

Scheme 6

II

In Scheme 7, compounds of the present invention of formula XXX can be readily prepared by reacting the methylthio intermediate XXXI with the amine NHRR, for example by heating the mixture preferably at a temperature greater than 100° C., more preferably 150-210° C. Alternatively, compounds of formula XXX can be readily prepared by reacting the methylsulfonyl intermediate XXXII with the amine NHRR, for example by heating the mixture preferably at a temperature greater than 40° C., more preferably 50-210° C.

Scheme 7

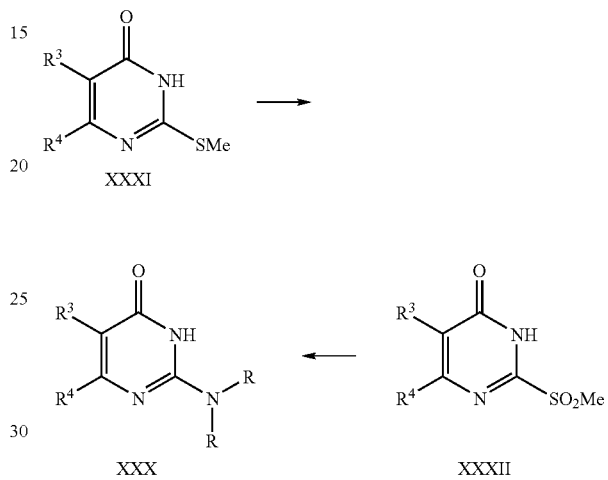

Amines of formula NHRR are commercially available or can be readily prepared by those skilled in the art from commercially available starting materials. For example, an amide, nitro or cyano group can be reduced under reducing conditions, such as in the presence of a reducing agent like lithium aluminum hydride and the like, to form the corresponding amine. Alkylation and acylation of amino groups are well known in the art. Chiral and achiral substituted amines can be prepared from chiral amino acids and amino acid amides (for example, alkyl, aryl, heteroaryl, cycloalkyl, arylalkyl, heteroarylalkyl, cycloalkylalkyl and the like substituted glycine, β-alanine and the like) using methods well known in the art, such as H. Brunner, P. Hankofer, U. Holzinger, B. Treittinger and H. Schoenenberger, Eur. J. Med. Chem. 25, 35-44, 1990; M. Freiberger and R. B. Hasbrouck, J. Am. Chem. Soc. 82, 696-698, 1960; Dornow and Fust, Chem. Ber. 87, 984, 1954; M. Kojima and J. Fujita, Bull. Chem. Soc. Jpn. 55, 1454-1459, 1982; W. Wheeler and D. O'Bannon, Journal of Labeled Compounds and Radiopharmaceuticals XXXI, 306, 1992; and S. Davies, N. Garrido, O. Ichihara and I. Walters, J. Chem. Soc., Chem. Commun. 1153, 1993.

Pyridones:

As displayed in Scheme 8, a suitable route to 2(1H)-pyridones III involves the cyclization reaction between an α,β-unsaturated ketone XXII and a sufficiently reactive, substituted acetamide in the presence of base (El-Rayyes and Al-Hajjar, *J. Heterocycyl. Chem.* 21, 1473 (1984)) and subsequent dehydrogenation.

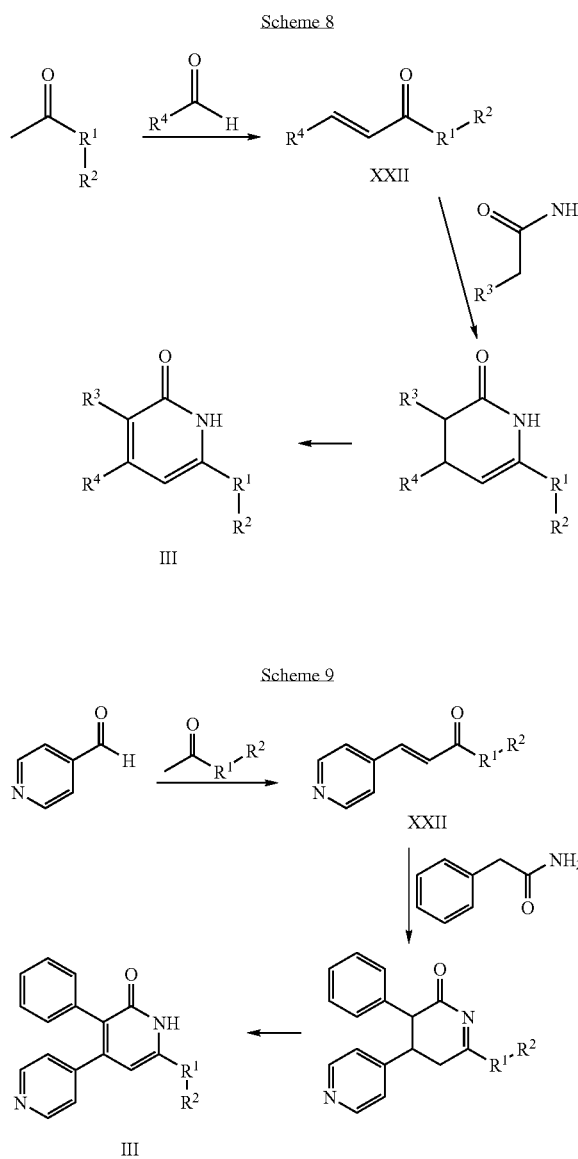

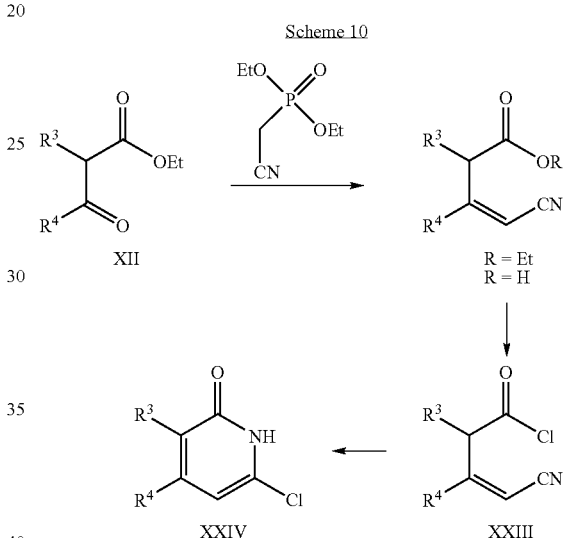

reacted with acetyl aryl, acetyl heteroaryl or acetyl cycloalkyl derivatives in the presence of piperidine/acetic acid at elevated temperature (Bayer and Hartmann, *Arch. Pharm.* (*Weinheim*) 324, 815 (1991)) as well as pinacolone ($CH_3$—$CO$—$C(CH_3)_3$) in the presence of sodium hydroxide to provide the unsaturated ketone XXII (or the analogous ketone from the corresponding heteroaromatic-4-carboxyaldehyde). The reaction of XXII with phenylacetamide in the presence of sodium ethoxide then may lead via the 3,4-dihydropyridone to 6-substituted 3-phenyl-4-(heteroaryl)-2(1H)-pyridones of structure III.

In Scheme 10, a feasible route is illustrated leading to 6-chloro-2(1H)-pyridone XXIV, a versatile intermediate for further modifications at the 6-position. This approach (G. Simchen, Chem. Ber. 103, 389-397 (1970) is based on the conversion of the unsaturated g-cyanocarboxylic acid chloride XXIII into XXIV in the presence of hydrogen chloride.

Accordingly (Scheme 9), pyridine-4-carboxaldehyde or other heteroaromatic carboxaldehyde-like pyrimidine-4-carboxaldehydes or quinoline-4-carboxyaldehydes may be reacted with acetyl aryl, acetyl heteroaryl or acetyl cycloalkyl Reaction of XXIV with ammonia (Katritzky and Rachwal, *J. Heterocylic Chem.* 32, 1007 (1995)), primary and secondary amines would lead to 2-amino substituted pyridones III.

In addition, pyridone III may be substituted at the N-1 position by reaction with, e.g., an alkyl halide in the presence of an appropriate base such as potassium carbonate.

An approach that may lead to a pyrimidinone of the general formula In is illustrated in Scheme 11.

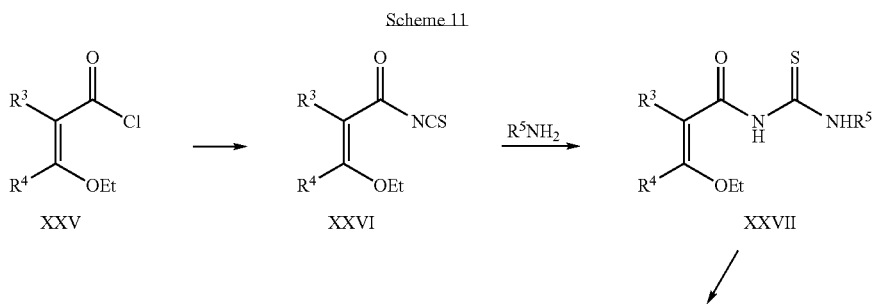

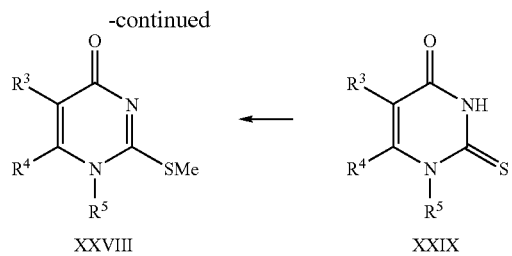

According to this approach (Shaw and Warrener, *J. Chem. Soc.* 153-156 (1958); Hronowski and Szarek, *Can. J. Chem.* 63, 2787 (1985); Agathocleous and Shaw, *J. Chem. Soc. Perkin Trans. I,* 2555 (1993)), an ethoxyacryloyl isothiocyanate XXVI is reacted with a primary amine to give as an addition product the acylthiourea XXVII which can be cyclized under basic or acidic conditions to the thiouracil compound XXVIII. XXVIII may be methylated to the methylthio derivative XXIX, a versatile intermediate for further transformations at the 2-position.

The following Examples are presented for illustrative purposes only and are not intended, nor should they be construed, as limiting the invention in any manner. Those skilled in the art will appreciate that modifications and variations of the compounds disclosed herein can be made without violating the spirit or scope of the present invention.

EXAMPLES

Example 1

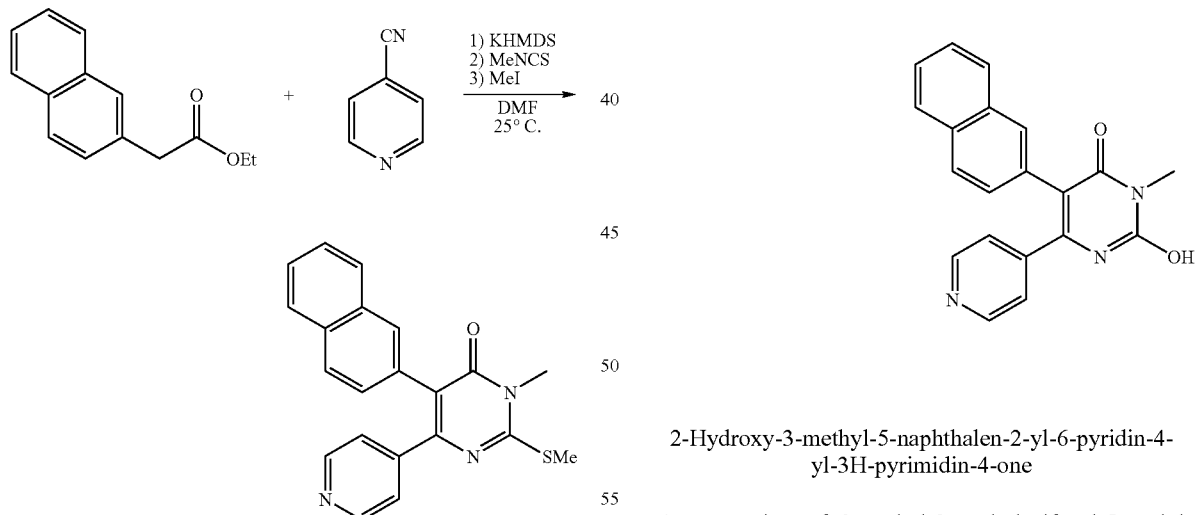

3-Methyl-2-methylsulfanyl-5-naphthalen-2-yl-6-pyridin-4-yl-3H-pyrimidin-4-one

To a stirring solution of ethyl-2-naphthylacetate (10.0 g, 46.7 mmol) and 4-cyanopyridine (4.86 g, 46.7 mmol) in 50 mL dry dimethylformamide (DMF) at room temperature under nitrogen was added 47 mL potassium tert-butoxide (1.0 M in 2-methyl-2-propanol) dropwise via syringe. The dark red solution was stirred at room temperature for 75 min. Methylthioisocyanate (3.41 g, 46.7 mmol) in 10 mL DMF added whole. The solution was stirred for 90 min at room temperature. Iodomethane (2.95 mL, 46.7 mmol) was added dropwise over a 3 min period. Solid precipitates out of reaction. Continued to stir as a mixture for 30 min. Water (500 mL) was slowly added to reaction mixture. The solid was collected via filtration then washed with water, cold ethanol (50 mL), and ether. The solid was air dried for 3 days. M+1=360.2.

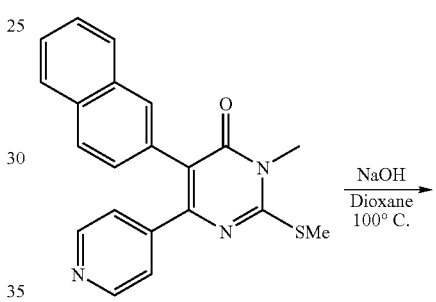

2-Hydroxy-3-methyl-5-naphthalen-2-yl-6-pyridin-4-yl-3H-pyrimidin-4-one

A suspension of 3-methyl-2-methylsulfanyl-5-naphthalen-2-yl-6-pyridin-4-yl-3H-pyrimidin-4-one (10.1 g, 28.1 mmol) was heated to 100° C. in 100 mL 1,4-dioxane and 60 mL 2.5M sodium hydroxide. After 7 h, TLC (95:5 DCM/MeOH) shows the solution to have no remaining starting material. The reaction was cooled to room temperature and acidified to pH 5 with 5M HCl. The resulting precipitate was collected by filtration, and then suspended in 100 mL hot methanol. The solid was cooled to room temperature then collected by filtration and washed with 100 mL diethylether. The product was air dried overnight to give a pale yellow solid. M+1=330.2.

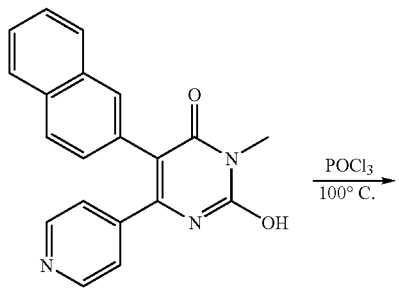

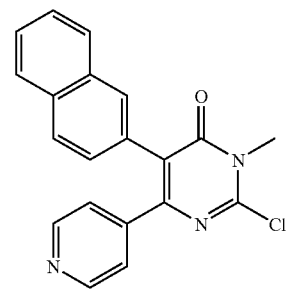

2-Chloro-3-methyl-5-naphthalen-2-yl-6-pyridin-4-yl-3H-pyrimidin-4-one

A suspension of 2-hydroxy-3-methyl-5-naphthalen-2-yl-6-pyridin-4-yl-3H-pyrimidin-4-one (10.0 g, 30.4 mmol) and phosphorous oxychloride (250 mL, 3 mol) was heated to 105° C. for 6 h to form a solution. Monitoring reaction by HPLC showed ~90% conversion. The reaction solution was cooled and the solvent removed under reduced pressure. Foam residue was dissolved in 500 mL 5% ethanol/chloroform. The organic layer was washed with 100 mL water three times and once with 100 mL 5% $NaHCO_3$. Organic dried over magnesium sulfate, then dried onto 30 g of silica. Final product purified on 400 g silica eluting with 0 to 2.5% methanol/dichloromethane to give a yellow solid. M+1=348.

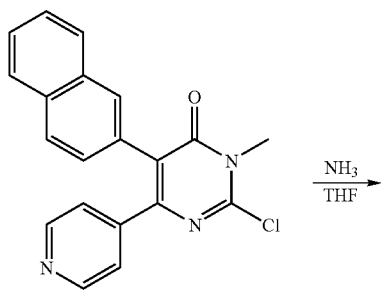

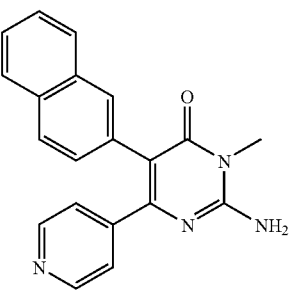

2-Amino-3-methyl-5-naphthalen-2-yl-6-pyridin-4-yl-3H-pyrimidin-4-one

Ammonia gas was bubbled through 80 mL of dry tetrahydrofuran at 0° C. for 15 min. To this solution was added 2-chloro-3-methyl-5-naphthalen-2-yl-6-pyridin-4-yl-3H-pyrimidin-4-one (400 mg; 1.18 mmol) whole. The solution was warmed to room temperature and stirred for 48 h. The tetrahydrofuran was removed under reduced pressure and the resulting solid partioned between 9:1 methylene chloride/ethanol and water. The organic layer was dried over $MgSO_4$, dried onto 4 g of silica, then purified on 10 g silica eluting with 0 to 5% methanol/dichloromethane to give the final product. M+1=329.2; NMR ($D_6MSO$) s (2H, 3.11 ppm), s (3H, 3.17 ppm), m (3H, 6.82-6.87 ppm), m (3H, 7.17-7.26 ppm), s (1H, 7.37 ppm), m (2H, 7.46-7.53 ppm), d (2H, 7.61 ppm), d (2H, 8.14 ppm).

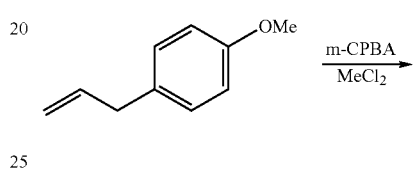

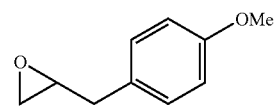

2-(4-Methoxybenzyl)-oxirane

To a stirring solution of 4-allylanisole (3.1 g, 20.9 mmol) in 50 mL dichloromethane was added 3-chloroperoxybenzoic acid (80%, 6.7 g, 31.4 mmol) at room temperature. TLC (20:1 hexanes/ethyl acetate) showed no remaining allyl after 3 h. The precipitate was removed via filtration and washed with hexanes. The filtrate was purified on 40 g silica eluting with 0 to 10% ethyl acetate/hexanes to give the product. NMR $CDCl_3$) d (1H, 2.55 ppm), m (2H, 2.7-2.8 ppm), dd (1H, 2.85 ppm), m (1H, 3.1 ppm), s (3H, 3.75 ppm), d (2H, 6.85 ppm), d (2H, 7.15 ppm).

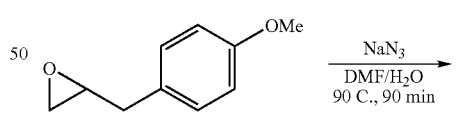

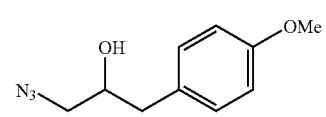

1-Azido-3-(4-methoxy-phenyl)-propan-2-ol

To a stirring solution of 2-(4-methoxy-benzyl)-oxirane (2.0 g, 12.2 mmol) in 10 mL DMF was added a solution of sodium azide (0.87 g, 13.4 mmol) in 2 mL water. The solution was heated to 90° C. for 90 min. The solvents were removed under reduced pressure and the resulting solid residue partitioned between ethyl acetate and water. The aqueous phase was washed three times with 10 mL ethyl acetate. The combined organic layers were dried over magnesium sulfate, then purified on 40 g silica eluting with 5-50% ethyl acetate/hexanes to give the product as a clear oil. NMR (CDCl$_3$) d (1H, 1.82 ppm), m (2H, 2.7-2.8 ppm), dd (1H, 3.25 ppm), dd (1H, 3.35 ppm), s (3H, 3.75 ppm), m (1H, 3.9-4.0 ppm), d (2H, 6.85 ppm), d (2H, 7.10 ppm).

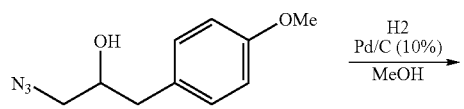

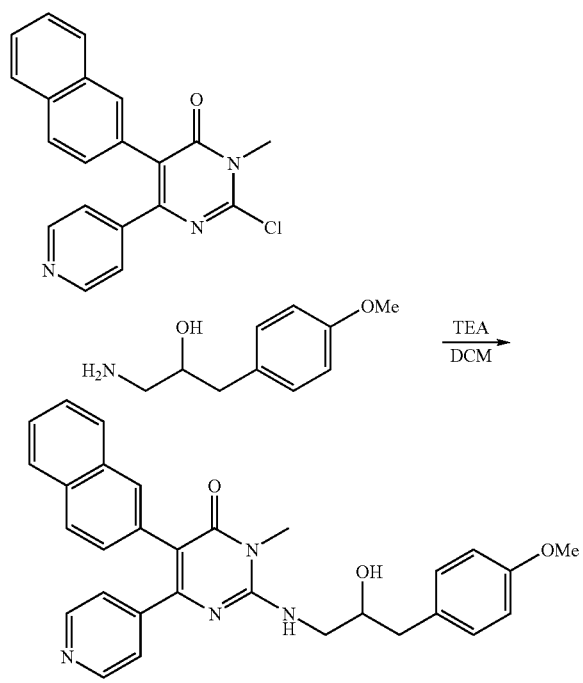

1-Amino-3-(4-methoxy-phenyl)-propan-2-ol

To a stirring solution of 1-azido-3-(4-methoxy-phenyl)-propan-2-ol (1.3 g, 6.3 mmol) in 50 mL methanol under a nitrogen atmosphere was added 10 mg of 10% Pd(OH)$_2$/C. The mixture was stirred under a balloon atmosphere of hydrogen for 18 h. The reaction mixture was filtered through a bed of celite, and the filtrate reduced to a clear oil under reduced pressure. M+1=170.

2-[2-Hydroxy-3-(4-methoxy-phenyl)-propylamino]-3-methyl-5-naphthalen-2-yl-6-pyridin-4-yl-3H-pyrimidin-4-one To a stirring solution of 1-amino-3-(4-methoxy-phenyl)-propan-2-ol (1.1 g, 6.1 mmol) and triethylamine in 25 mL dichloromethane was added 2-chloro-3-methyl-5-naphthalen-2-yl-6-pyridin-4-yl-3H-pyrimidin-4-one. The solution was stirred at room temperature for 72 h. The organic layer was washed twice with 5% sodium bicarbonate, once with brine, then dried over magnesium sulfate. The product was purified on 90 g of silica eluting with 1 to 5% methanol/dichloromethane to give a yellow foam. M+1=493.2.

Example 2

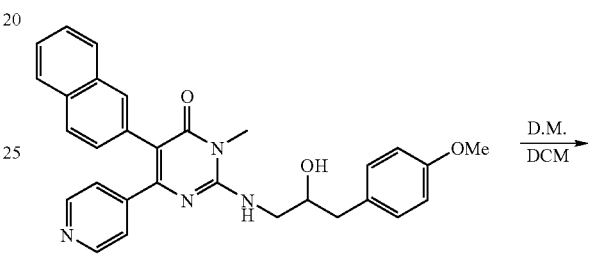

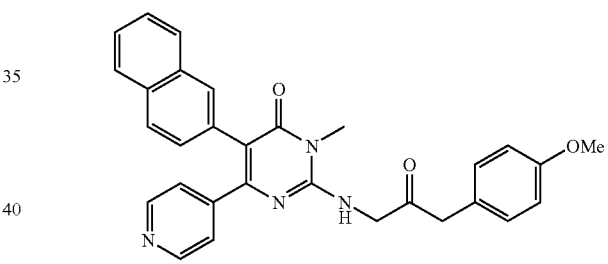

2-[3-(4-Methoxy-phenyl)-2-oxo-propylamino]-3-methyl-5-naphthalen-2-yl-6-pyridin-4-yl-3H-pyrimidin-4-one To a stirring solution of 2-[2-hydroxy-3-(4-methoxy-phenyl)-propylamino]-3-methyl-5-naphthalen-2-yl-6-pyridin-4-yl-3H-pyrimidin-4-one (765 mg, 1.55 mmol) in 20 mL dichloromethane was added Dess-Martin Periodinane (660 mg, 1.55 mmol). The dark red solution was stirred for 18 h at room temperature. The reaction mixture was diluted with 80 mL dichloromethane and washed twice with 15 mL 5% sodium bicarbonate, and dried over magnesium sulfate. The product was purified on 40 g silica eluting with 0 to 4% methanol/dichloromethane to provide the product as a yellow foam. The product was further purified on reverse phase high performance chromatography using an water/acetonitrile (0.1% TFA) gradient. The final sample was lyophilized from 50% acetonitrile/water to give a yellow powder. M+1=491.2.

Example 3

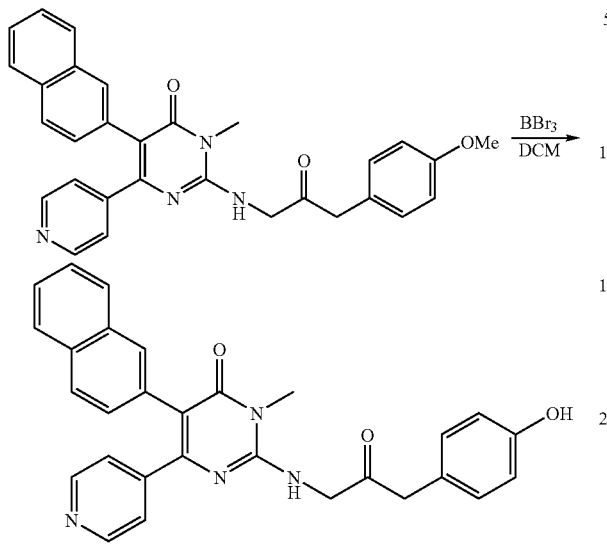

2-[3-(4-Hydroxy-phenyl)-2-oxo-propylamino]-3-methyl-5-naphthalen-2-yl-6-pyridin-4-yl-3H-pyrimidin-4-one To a chilled (0° C.) stirring solution of 2-[3-(4-methoxy-phenyl)-2-oxo-propylamino]-3-methyl-5-naphthalen-2-yl-6-pyridin-4-yl-3H-pyrimidin-4-one (250 mg, 0.21 mmol) in 20 mL dichloromethane under an atmosphere of nitrogen was added boron tribromide (39 μL, 0.42 mmol) in 0.4 mL of dichloromethane. The resulting precipitate was stirred for 18 h warming to room temperature. The solvent was removed under reduced pressure, then the product was dissolved in 4 mL methanol. The product was purified on on reverse phase high performance chromatography eluting with a water/acetonitrile (0.1% TFA) gradient. The final product was lyophilized from 50% acetonitrile/water to give a yellow powder. M+1=477.2 NMR (CD$_3$CN/D$_2$O 3:1) s (3H, 3.40 ppm), s (2H, 3.60 ppm), s (2H, 4.25 ppm), d (2H, 6.51 ppm), d (2H, 6.95 ppm), d (1H, 7.22 ppm), m (3H, 7.4-7.5 ppm), d (2H, 7.5 ppm), d (1H, 7.72 ppm), d (1H, 7.78), d (2H, 8.30 ppm).

Example 4

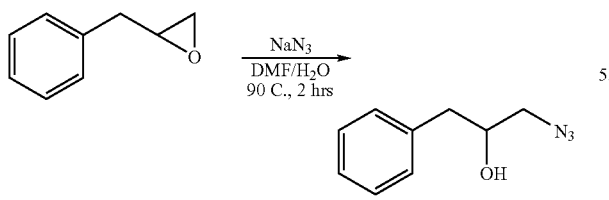

1-Azido-3-phenyl-propan-2-ol

To the stirring solution of (2,3-epoxypropyl)benzene (1.0 g, 7.5 mmol) in 4 mL DMF was added a solution of sodium azide (0.97 g, 15 mmol) in 4 mL water. The solution was heated to 90° C. for 1 h. The solvent was removed under reduced pressure. The solid residue was partitioned between ethyl acetate and near saturated sodium chloride. The aqueous layer was washed three times with ethyl acetate. The combined organic layers were dried over magnesium sulfate, and purified on 10 g of silica eluting with 0 to 50% ethyl acetate/hexanes to give a clear oil. NMR (CDCL$_3$) d (1H, 1.97 ppm), m (2H, 2.73-2.82 ppm), m (1H, 3.22-3.30 ppm), dd (1H, 3.36 ppm), m (1H, 3.92-4.02 ppm), m (3H, 7.13-7.28 ppm), m (2H, 7.28-7.34 ppm).

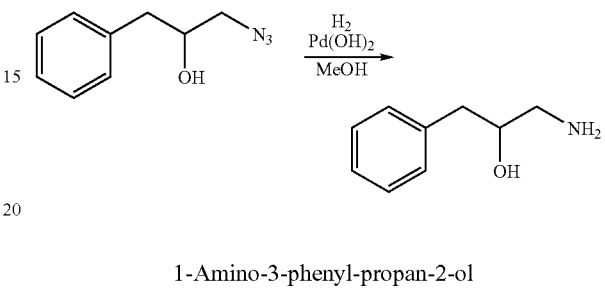

1-Amino-3-phenyl-propan-2-ol

To a stirring solution of 1-azido-3-phenyl-propan-2-ol (590 mg, 3.4 mmol) in 20 mL methanol under a nitrogen atmosphere was added 10 mg of Pd(OH)$_2$/C (10%). Hydrogen gas was delivered via balloon. The solution was stirred overnight at room temperature. The catalyst was removed by filtering the solution through a bed of celite, and the filtrate was concentrated to give a clear oil under reduced pressure. M+1=152.

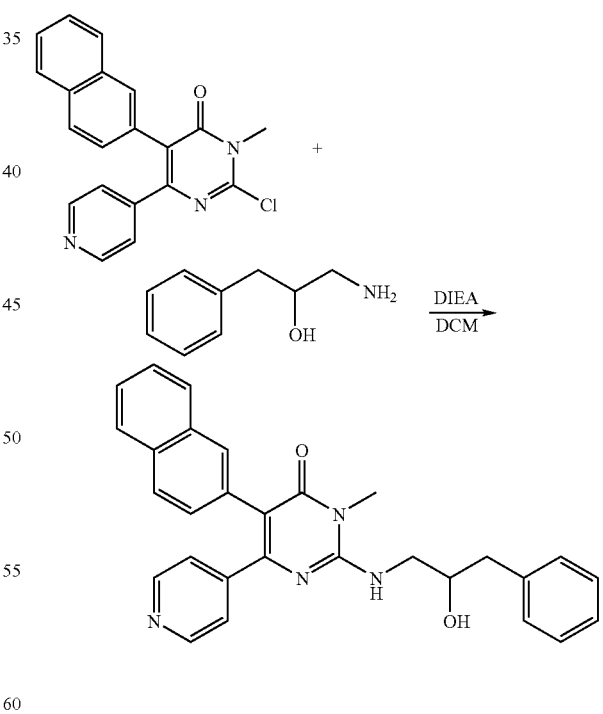

2-(2-Hydroxy-3-phenyl-propylamino)-3-methyl-5-naphthalen-2-yl-6-pyridin-4-yl-3H-pyrimidin-4-one To a stirring solution of 1-amino-3-phenyl-propan-2-ol (0.51 g, 3.3 mmol) and triethylamine (0.45 mL, 3.3 mmol) in 20 mL dichloromethane was added (0.92 g, 2.6 mmol) 2-chloro-3-methyl-5-naphthalen-2-yl-6-pyridin-4-yl-3H- pyrimidin-4-one. The solution was stirred for 18 h at room temperature. The solution was diluted with ethyl acetate and washed with 5% sodium bicarbonate. The organic layer was dried over magnesium sulfate and purified on 10 g silica eluting product with 0 to 5% methanol/dichloromethane to give a pale yellow solid. M+1=463.2.

Example 5

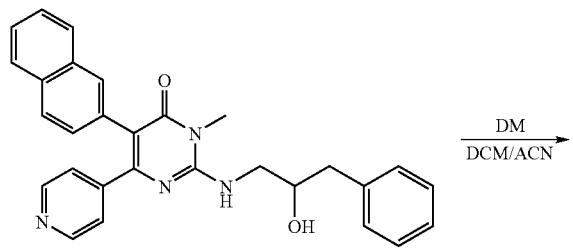

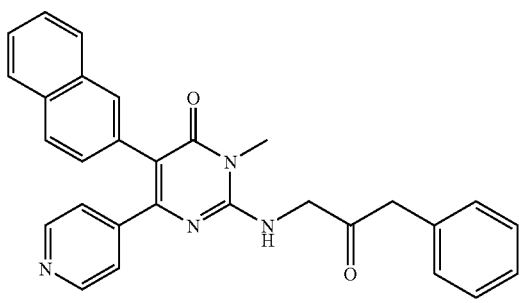

3-Methyl-5-naphthalen-2-yl-2-(2-oxo-3-phenyl-propylamino)-6-pyridin-4-yl-3H-pyrimidin-4-one To a striring suspension of 2-(2-hydroxy-3-phenyl-propylamino)-3-methyl-5-naphthalen-2-yl-6-pyridin-4-yl-3H-pyrimidin-4-one (150 mg, 0.32 mmol) in 5 mL dry acetonitrile and 5 mL dichloromethane was added Dess-Martin Periodinane (206 mg, 0.49 mmol). The reaction mixture turned to an orange color within 3 min. After 30 min, TLC (95:5 dichloromethane/methanol) showed approximately 15% of the starting material remained. More Dess-Martin Periodinane (50 mg, 0.12 mmol) was added and the reaction was stirred for and additional 30 min. The curde product was purified on 10 g silica eluting with 0 to 3% methanol/dichloromethane to give a clear film. The material was further purified on reverse phase high performance chromatography eluting with water/acetonitrile (0.1% TFA) gradient. The final material was lyophilized from 50% acetonitrile/water to give a pale yellow powder. M+1=461.3. NMR (CD$_3$CN/D$_2$O 3:1) s (3H; 3.5 ppm), s (2H; 3.8 ppm), s (2H; 4.3 ppm), dd (2H; 7.15 ppm), m (4H, 7.2-7.3 ppm), m (3H, 7.45-7.55 ppm), d (2H, 7.62 ppm), d (1H, 7.72 ppm), d (1H, 7.84 ppm), d (1H, 7.88 ppm), d (2H, 8.39 ppm). M+1=461.2.

Example 6

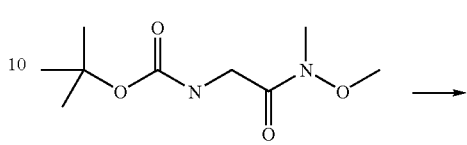

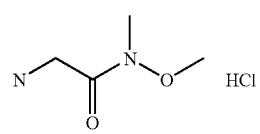

Glycine N'-methoxy-N'-methylamide hydrochloride

To a saturated HCl solution in ether (50 mL) at room temperature was added N-(tert-butoxycarbonyl)glycine-N'-methoxy-N'-methylamide (10 g, 46 mmol). The solution was stirred for 5 h and evaporated to give a sticky residue.

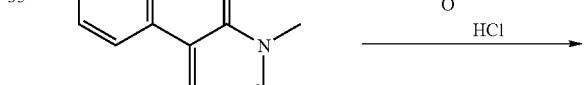

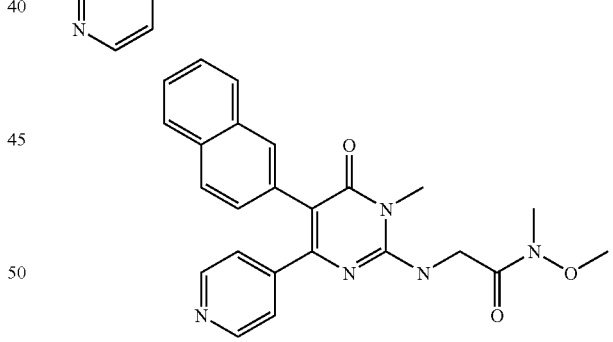

2-(N'-Methoxy-N'-methylaminocarbonylmethylamino)-3-methyl-5-naphthalen-2-yl-6-pyridin-4-yl-3H-pyrimidin-4-one Glycine N'-methoxy-N'-methylamide hydrochloride (378 mg, 2.45 mmol) and sodium carbonate (0.40 g, 3.8 mmol) in NMP (5 mL) were stirred at room temperature for 5 min. 2-Chloro-3-methyl-5-naphthalen-2-yl-6-pyridin-4-yl-3H-pyrimidin-4-one (345 mg, 1 mmol) was then added. After stirring for 3 h, ethyl acetate (60 mL) was added. The solution was washed with brine (3×50 mL), dried (sodium sulfate), filtered, and evaporated to give the crude product. M+1=430.3

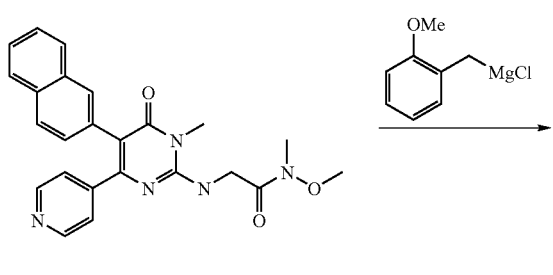 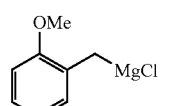 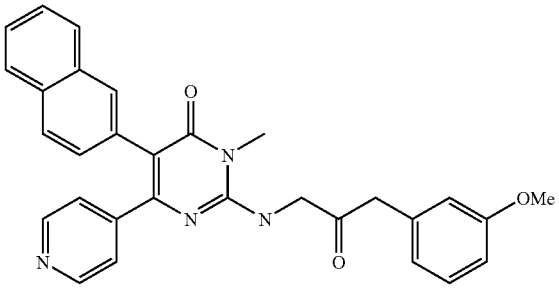

2-[3-(3-Methoxy-phenyl)-2-oxo-propylamino]-3-methyl-5-naphthalen-2-yl-6-pyridin-4-yl-3H-pyrimidin-4-one To a solution of 2-(N'-methoxy-N'-methylaminocarbonyl-methylamino)-3-methyl-5-naphthalen-2-yl-6-pyridin-4-yl-3H-pyrimidin-4-one (400 mg, 0.93 mmol) in THF (10 mL) at 0° C. was slowly added 3-methoxybenzylmagnesium chloride (Rieke Metal, 0.25 M in THF, 20 mL). After 3 h, water (100 mL) and ethyl acetate (200 mL) were added. The layers were separated. The organic layer was washed with brine (3×80 mL), dried, and evaporated to give crude product. Column chromatograph purification (silica gel, 1-2% MeOH/CH$_2$Cl$_2$) gave the product as a solid. M+1=491.2.

Example 8

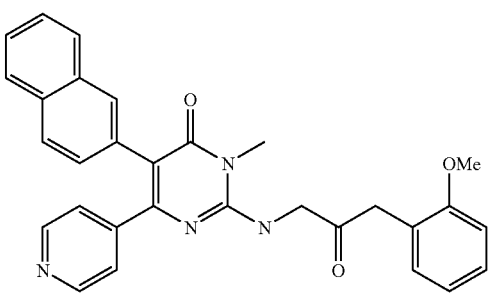

2-[3-(2-Methoxy-phenyl)-2-oxo-propylamino]-3-methyl-5-naphthalen-2-yl-6-pyridin-4-yl-3H-pyrimidin-4-one To the crude product obtained above (500 mg, approximately 1 mmol) THF (7 mL) at 0° C. was slowly added 2-methoxybenzylmagnesium chloride (Rieke Metal, 0.25 M in THF, 25 mL). After 1 h, water (100 mL) and ethyl acetate (200 mL) were added. The layers were separated. The organic layer was washed with brine (3×80 mL), dried, and evaporated to give the crude product. Column chromatograph purification (silica gel, 1-2% MeOH/CH2Cl2) gave the product. M+1=491.2.

Example 7

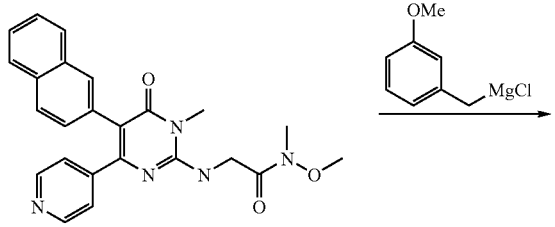 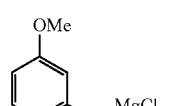

2-[3-Phenyl-2-oxo-propylamino]-3-methyl-5-naphthalen-2-yl-6-pyridin-4-yl-3H-pyrimidin-4-one To a solution of 2-(N'-methoxy-N'-methylaminocarbonyl-methylamino)-3-methyl-5-naphthalen-2-yl-6-pyridin-4-yl-3H-pyrimidin-4-one (1.46 g, 3.4 mmol) in THF (30 mL) at 0° C. was slowly added benzylmagnesium chloride (Aldrich, 2.5M in THF, 20 mL). After 2 h, water (100 mL) and ethyl acetate (200 mL) were added. The layers were separated. The organic layer was washed with brine (3×80 mL), dried, and evaporated to give the crude product. Column chromatograph purification (silica gel, 1-2% MeOH/CH$_2$Cl$_2$) gave the final product. M+1=491.2.

Example 9

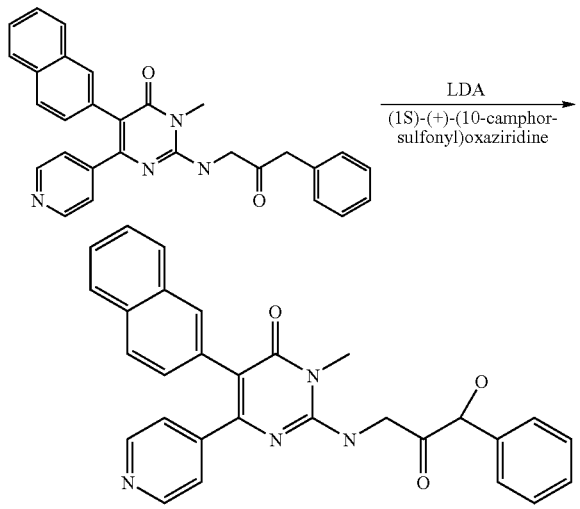

2-[3-Phenyl-2-hydroxy-propylamino]-3-methyl-5-naphthalen-2-yl-6-pyridin-4-yl-3H-pyrimidin-4-one To a solution of 2-[3-phenyl-2-oxo-propylamino]-3-methyl-5-naphthalen-2-yl-6-pyridin-4-yl-3H-pyrimidin-4-one (123 mg, 0.27 mmol) in THF (5 mL) at −78° C. was added LDA (Aldrich, 2.0 M in THF, 0.4 mL). The mixture was stirred for 1 h. Lithium chloride (30 mg) was added. After 5 minutes, (1S)-(+)-(10-camphorsulfonyl)oxaziridine (200 mg, 0.87 mmol) was added. The mixture was stirred at −78 for 2 hours, and quenched with water (5 mL) and ethyl acetate (80 mL). The solution was washed with brine (3×50 mL), dried, and evaporated. The crude product was purified by preparative TLC (6% MeOH/CH2Cl2). 8 mg (7%) solids. M+1=477.2.

Example 10

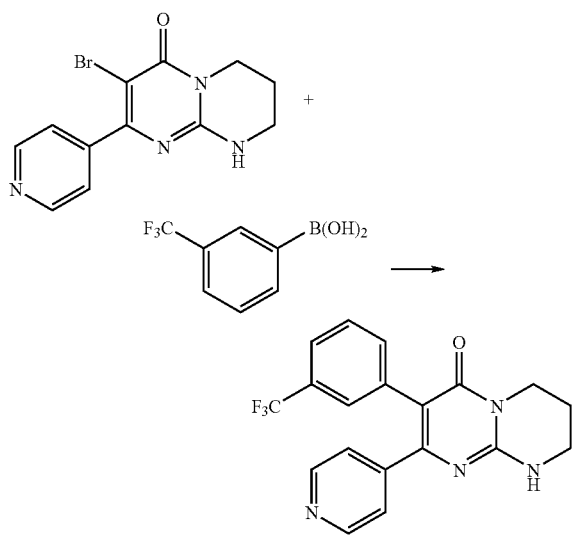

2-Pyridin-4-yl-3-(3-trifluoromethyl-phenyl)-6,7,8,9-tetrahydro-pyrimido[1,2-a]pyrimidin-4-one A mixture of 3-Bromo-2-pyridin-4-yl-6,7,8,9-tetrahydro-pyrimido[1,2-a]pyrimidin-4-one (0.62 g, 2.0 mmol), the boronic acid (0.62 g, 3.26 mmol), Pd$_2$dba$_3$ (0.53 g, 0.58 mmol), Ph$_3$P (0.30 g, 1.14 mmol), and K$_3$PO$_4$ (0.85 g, 4.0 mmol) in THF (15 mL) was heated at 100° C. in a sealed tube for 20 h. The cooled mixture was treated with CH$_2$Cl$_2$—NaHCO$_3$ (aq) and the organic phase was concentrated. Purification on a reverse phase HPLC afforded the product as a solid (300 mg, 40%). M+1 273.

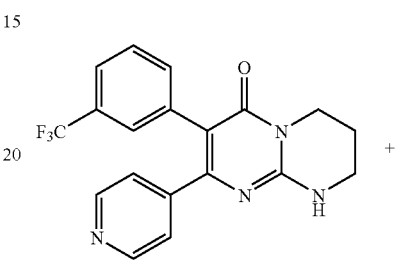

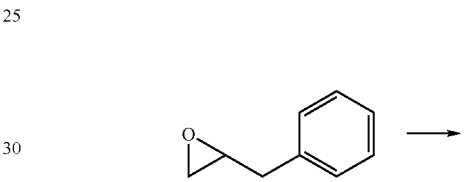

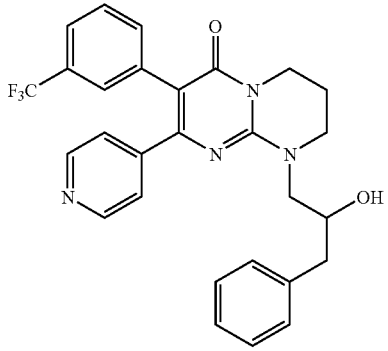

9-(2-Hydroxy-3-phenyl-propyl)-2-pyridin-4-yl-3-(3-trifluoromethyl-phenyl)-6,7,8,9-tetrahydro-pyrimido[1,2-a]pyrimidin-4-one To a 50 mL RBF was charged 2-pyridin-4-yl-3-(3-trifluoromethyl-phenyl)-6,7,8,9-tetrahydro-pyrimido[1,2-a]pyrimidin-4-one (140 mg, 0.37 mmol), 2-benzyl-oxirane (135 mg, 0.63 mmol), and LiHMDS (1M, 1.0 mL) under N$_2$. The mixture was heated at 90 C for 4 h and then cooled to room temperature. The content was diluted with H$_2$O, and extracted with dichlorometane three times. The combined organic phase was dried with Na$_2$SO$_4$, concentrated under vacuum. Flash chromatography on silica with 0-5% (2N NH$_3$-MeOH)/CH$_2$Cl$_2$ afforded the product (3) as a white solid (110 mg, 58%). M+1 507.

Example 11

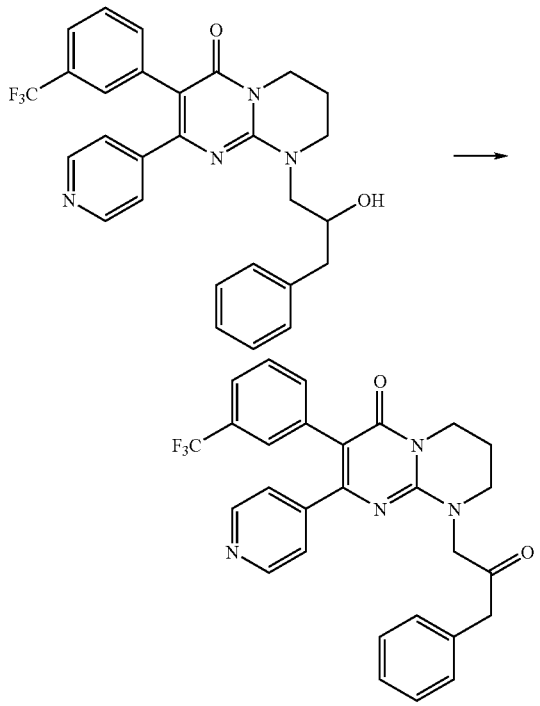

9-(2-Oxo-3-phenyl-propyl)-2-pyridin-4-yl-3-(3-trifluoromethyl-phenyl)-6,7,8,9-tetrahydro-pyrimido[1,2-a]pyrimidin-4-one A solution of 9-(2-hydroxy-3-phenyl-propyl)-2-pyridin-4-yl-3-(3-trifluoromethyl-phenyl)-6,7,8,9-tetrahydro-pyrimido[1,2-a]pyrimidin-4-one (50 mg, 0.1 mmol) in $CH_2Cl_2$ (5 mL) was treated with the Dess Martin Periodinane (450 mg, 1.1 mmol). After the mixture was stirred at room temperature for 5 hr, the mixture was washed with $NaHCO_3$ (aq). The organic residue was loaded to a silica column and eluted with 0-4% (2N $NH_3$-MeOH)/$CH_2Cl_2$. The product (4) was collected as a yellow solid (35 mg, 70%). M+1 505.

Example 12

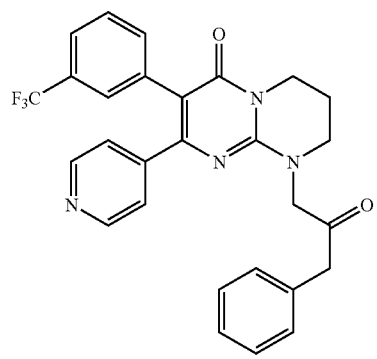

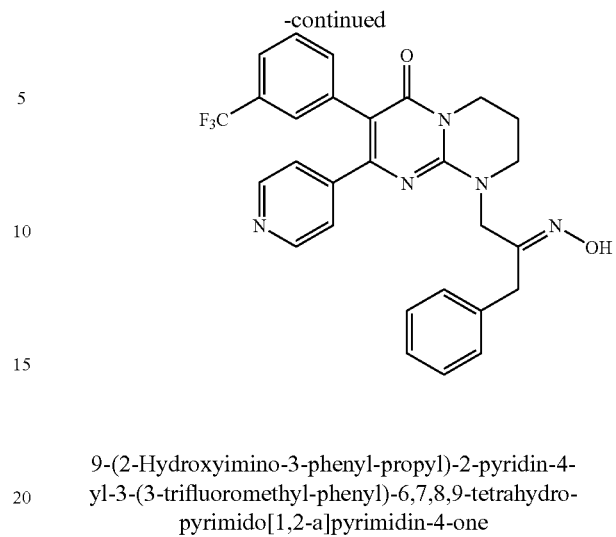

9-(2-Hydroxyimino-3-phenyl-propyl)-2-pyridin-4-yl-3-(3-trifluoromethyl-phenyl)-6,7,8,9-tetrahydro-pyrimido[1,2-a]pyrimidin-4-one A mixture of the 9-(2-Oxo-3-phenyl-propyl)-2-pyridin-4-yl-3-(3-trifluoromethyl-phenyl)-6,7,8,9-tetrahydro-pyrimido[1,2-a]pyrimidin-4-one (35 mg) and NH2OH—HCl (35 mg) in EtOH (5 mL) was heated at 70 C for 1 hr. The cooled mixture was evaporated and the crude residue was partitioned between $NaHCO_3$ (aq) and $CH_2Cl_2$. The organic phase was concentrated and eluted on silica with 1-8% (2N $NH_3$-MeOH)/$CH_2Cl_2$ to afford th eproduct (5) as a yeloow solid (35 mg, 98%). M+1 520.

Example 13

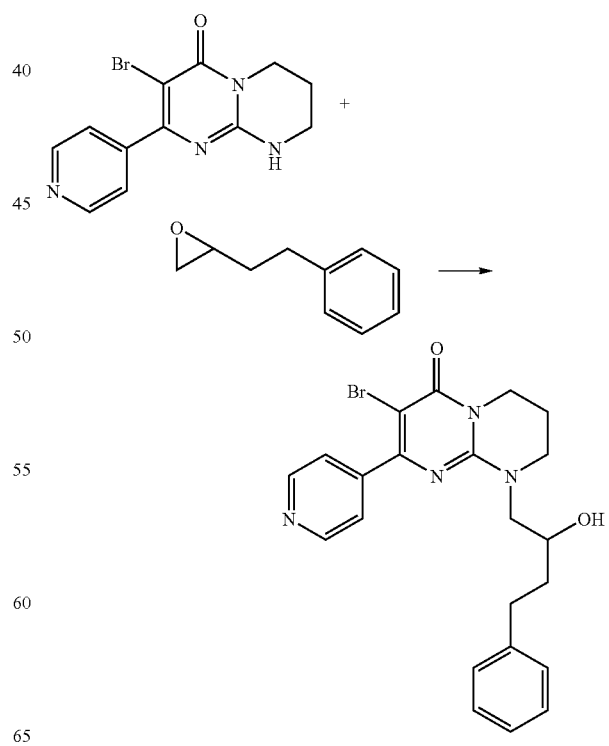

Bromo-9-(2-hydroxy-4-phenyl-butyl)-2-pyridin-4-yl-6,7,8,9-tetrahydro-pyrimido[1,2-a]pyrimidin-4-one A mixture of 3-Bromo-2-pyridin-4-yl-6,7,8,9-tetrahydro-pyrimido[1,2-a]pyrimidin-4-one (0.45 g, 1.46 mmol) and 2-Phenethyl-oxirane (0.65 g, 4.4 mmol) in DMF (20 mL) was treated LiHMDS (5 mL, 5 mml). The mixture was heated at 90 C for 1 h and was cooled to room temperature. Saturated NH$_4$Cl (50 mL) was added and the mixture was extracted with CH$_2$Cl$_2$ (3×20 mL). The organic phase was washed with H2O (3×), dried (Na$_2$SO$_4$), and concentrated. The resulting brown oil was chromatographed on silica with 1-5% (2N NH$_3$-MeOH)/CH$_2$Cl$_2$ to afford the product as a white solid. M+1 457.

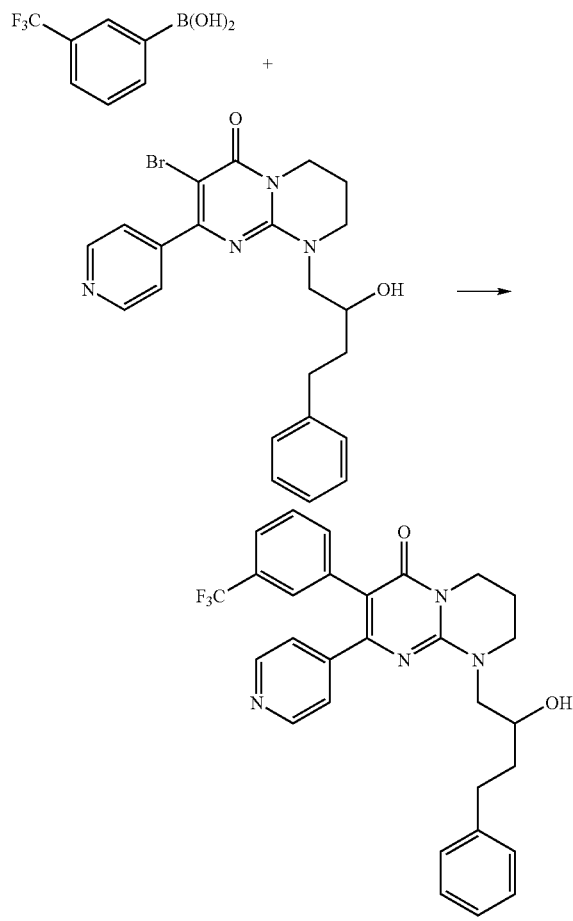

9-(2-Hydroxy-4-phenyl-butyl)-2-pyridin-4-yl-3-(3-trifluoromethyl-phenyl)-6,7,8,9-tetrahydro-pyrimido[1,2-a]pyrimidin-4-one A mixture the boronic acid (187 mg, 0.98 mmol), and 3-Bromo-9-(2-hydroxy-4-phenyl-butyl)-2-pyridin-4-yl-6,7,8,9-tetrahydro-pyrimido[1,2-a]pyrimidin-4-one (211 mg, 0.46 mmol) in dioxane (8 mL) was treated with Pa$_2$(dba)$_3$ (40 mg, 0.043 mmol), Ph$_3$P (60 mg, 0.23 mmol), and K$_3$PO$_4$ (308 mg, 1.45 mmol) under N$_2$. The mixture was heated at 90 C for 4 hr and then cooled to room temperature. Filtration through a Celite pad with CH$_2$Cl$_2$ washings and concentration of the filtrate resulted in an orange oil. This was eluted on silica with 0-5% (2N NH3-MeOH in CH$_2$Cl$_2$) to afford the product as a yellow solid (278 mg from a total of 289 mg bromide, 84%). M+1 521.

Example 14

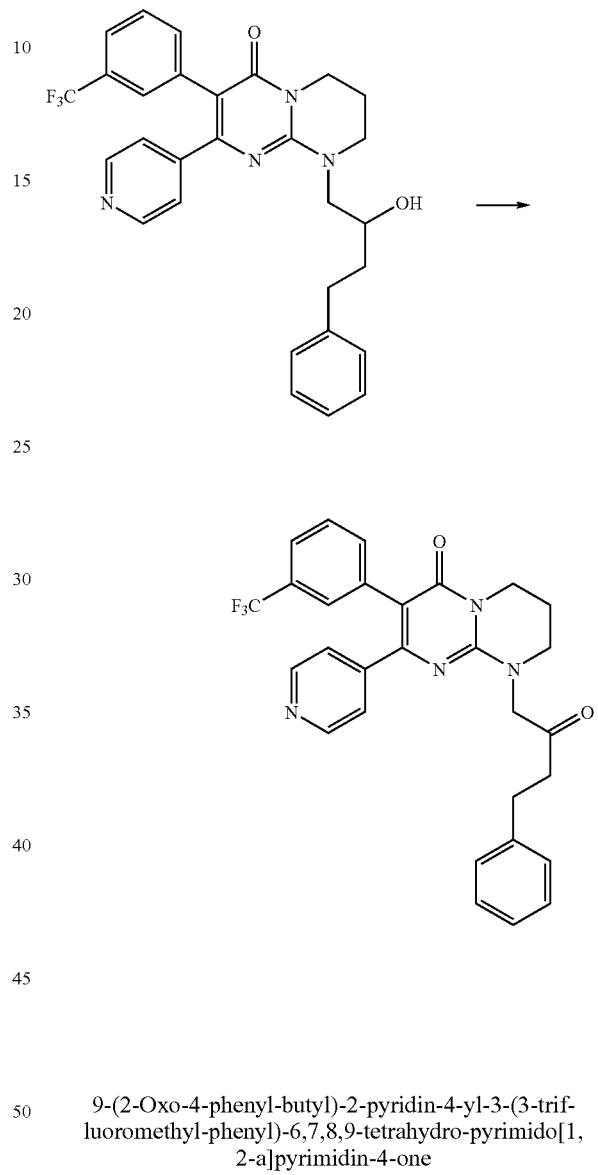

9-(2-Oxo-4-phenyl-butyl)-2-pyridin-4-yl-3-(3-trifluoromethyl-phenyl)-6,7,8,9-tetrahydro-pyrimido[1,2-a]pyrimidin-4-one A solution of DMSO (0.25 mL, 3.5 mmol) in CH$_2$Cl$_2$ (10 mL) at –78 C was treated with a solution of oxallyl chloride (2N in CH$_2$Cl$_2$, 0.8 mL, 1.6 mmol) dropwise. After stirring for 15 min, a solution of 9-(2-hydroxy-4-phenyl-butyl)-2-pyridin-4-yl-3-(3-trifluoromethyl-phenyl)-6,7,8,9-tetrahydro-pyrimido[1,2-a]pyrimidin-4-one (227 mg, 0.43 mmol) in CH$_2$Cl$_2$ (15 mL) was added. The mixture was stirred at –60 C for 15 min before a solution of Et3N (0.5 mL, 3.6 mmol) in CH$_2$Cl$_2$ (3 mL) was added. The reaction mixture was allowed to warm to room temperature overnight and was washed with NaHCO$_3$ (aq). The organic layer was dired (Na$_2$SO$_4$), and concentrated. The residue was eluted on silica gel with 0-5% (2N NH3-MeOH in CH$_2$Cl$_2$) to afford the product as a light yellow solid (148 mg, 63%). M+1 519.

Example 15

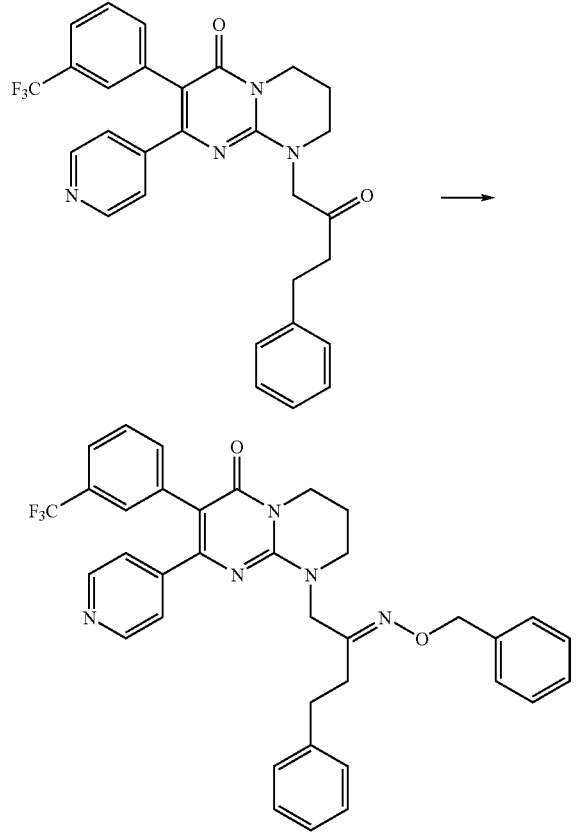

9-(2-Benzyloxyimino-4-phenyl-butyl)-2-pyridin-4-yl-3-(3-trifluoromethyl-phenyl)-6,7,8,9-tetrahydro-pyrimido[1,2-a]pyrimidin-4-one A solution of BnONH$_2$—HCl (68 mg, 0.43 mmol) and 9-(2-Benzyloxyimino-4-phenyl-butyl)-2-pyridin-4-yl-3-(3-trifluoromethyl-phenyl)-6,7,8,9-tetrahydro-pyrimido[1,2-a] pyrimidin-4-one (65 mg, 0.12 mmol) in EtOH (5 mL) was heated at 70 C for 1 hr. The cooled mixture was partitioned between CH$_2$Cl$_2$ and NaHCO$_3$ (5% aq.) and organic phase was dried (Na$_2$SO$_4$) and concentrated. Flash chromatography on silica gel (0-5% 2N NH3-MeOH in CH$_2$Cl$_2$ afforded the product. M+1 624.

Example 16

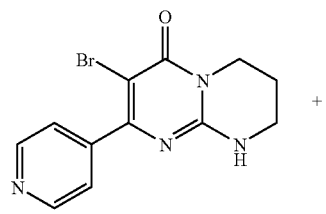

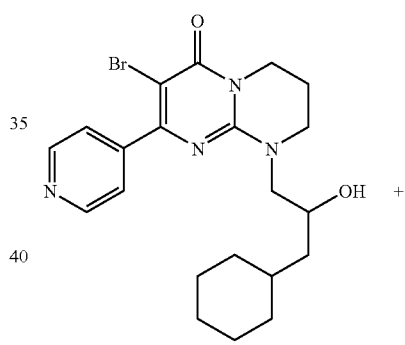

3-Bromo-9-(3-cyclohexyl-2-hydroxy-propyl)-2-pyridin-4-yl-6,7,8,9-tetrahydro-pyrimido[1,2-a]pyrimidin-4-one This compound was prepared in a similar fashion as described earlier using LiHMDS in DMF in 50% yield (660 mg product from 900 mg starting material). M+1 447,449.

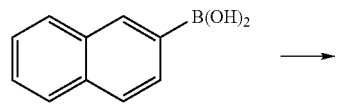

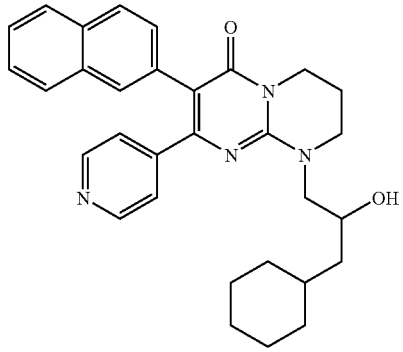

(3-Cyclohexyl-2-hydroxy-propyl)-2-pyridin-4-yl-3-(3-trifluoromethyl-phenyl)-6,7,8,9-tetrahydro-pyrimido[1,2-a]pyrimidin-4-one A mixture of the bromide (0.66 g, 1.5 mmol) and the boronic acid (0.64 g, 3.7 mmol) in dioxane (20 mL) was treated with Pd$_2$dba$_3$ (0.27 g, 0.3 mmol), Ph$_3$P (0.16 g, 0.6 mmol), and K3PO4 (1.9 g, 8.9 mmol) under nitrogen. The mixture was heated at 95 C overnight and was then cooled to room temperature. The mixture was filtered through a pad of Celite with CH$_2$Cl$_2$ washing. The combined filtrate was concentrated and the residue was eluted on silica with 0-5% (2N NH3-MeOH in CH$_2$Cl$_2$) to afford the product as a yellow foam. M+1 495.

Example 17

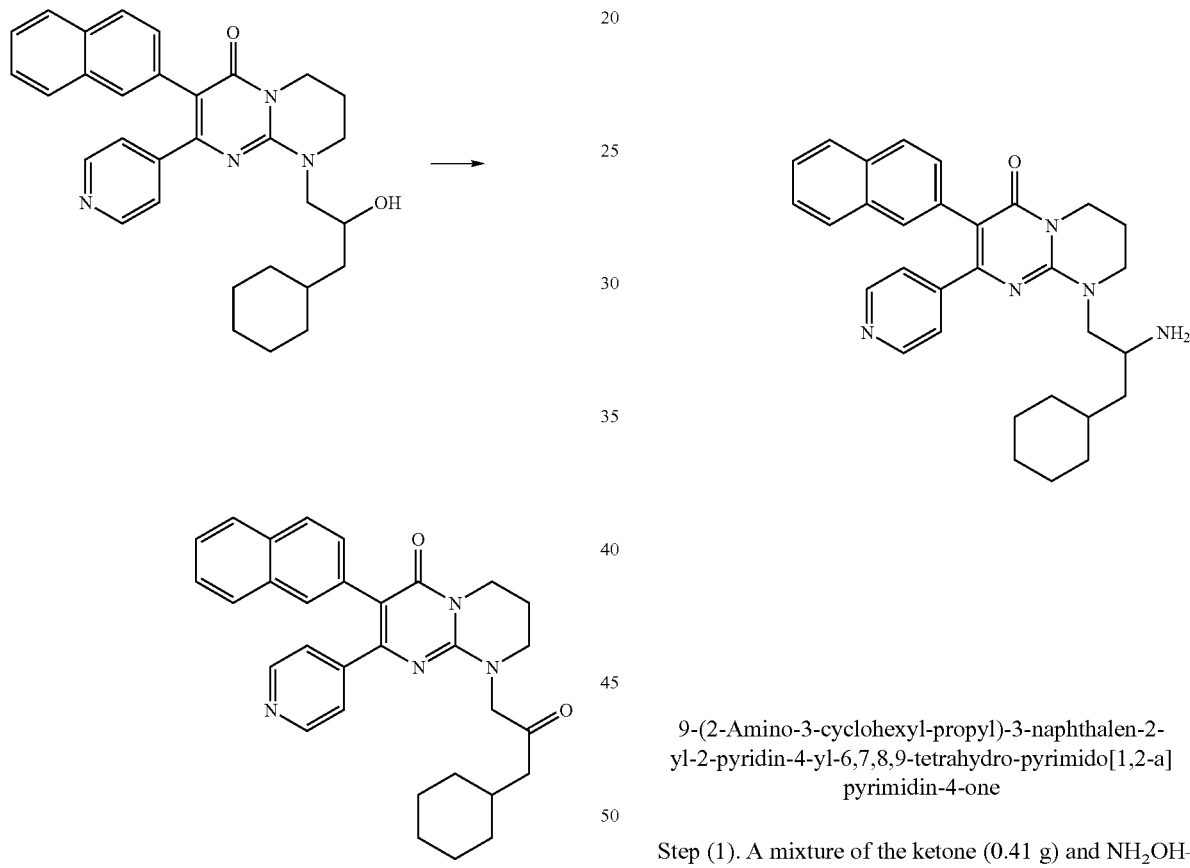

9-(3-Cyclohexyl-2-oxo-propyl)-2-pyridin-4-yl-3-(3-trifluoromethyl-phenyl)-6,7,8,9-tetrahydro-pyrimido[1,2-a]pyrimidin-4-one This compound was prepared under Swern conditions as described earlier in 89% (0.41 g from 0.46 g starting material). M+1 492.

Example 18

9-(2-Amino-3-cyclohexyl-propyl)-3-naphthalen-2-yl-2-pyridin-4-yl-6,7,8,9-tetrahydro-pyrimido[1,2-a]pyrimidin-4-one Step (1). A mixture of the ketone (0.41 g) and NH$_2$OH—HCl (0.4 g) in EtOH (15 mL) was heated at 70 C for 1 h. The solvent was evaporated and the residue was partitioned between CH$_2$Cl$_2$—NaHCO$_3$. The organic phase was concentrated and used for the next reaction.

Step (2) The crude product from step (1) was dissolved in dioxane (30 mL) and treated with Raney-Ni (R-2400, 2.0 g). The mixture was heated at 95 C with vigorous stirring for 1 hr. The mixture was filtered through a pad of Celite with washings (2N NH3-MeOH, 3×). The combined filtrate was concentrated and was partitioned between CH$_2$Cl$_2$—NH3(aq) (50 mL each). The organic phase was separated and concentrated. The residue was eluted on silica with 0-8% (2N NH3-MeOH in DCM) to afford the product as a yellow foam (0.16 g, 38%). M+1 494.

Example 19

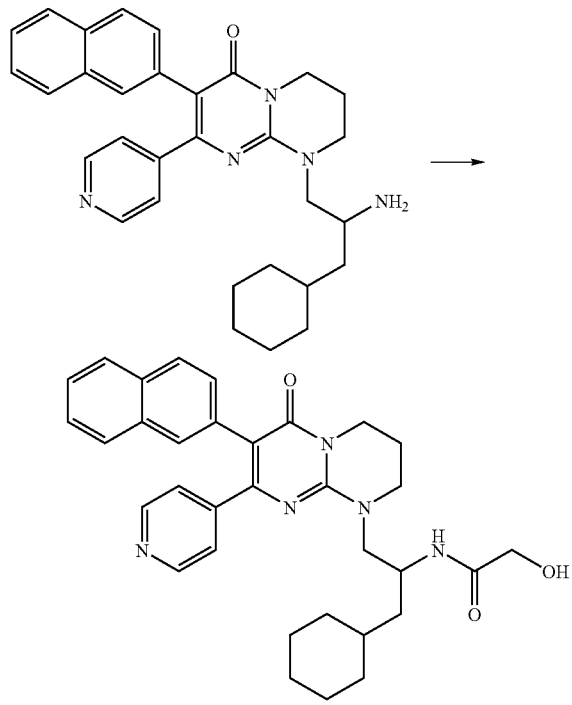

N-[1-Cyclohexylmethyl-2-(7-naphthalen-2-yl-6-oxo-8-pyridin-4-yl-3,4-dihydro-2H,6H-pyrimido[1,2-a]pyrimidin-1-yl)-ethyl]-2-hydroxy-acetamide A mixture of the amine (33 mg, 0.07 mmol), 2-hydroxy-acetic acid (50 mg), EDCI-HCl (90 mg), and HOAt (90 mg) in $CH_2Cl_2$ (3 mL) was stirred for 2 hrs. $H_2O$ (5 mL) was added and the mixture was extracted with EtOAc (20 mL). The organic phase was washed with $H_2O$ (3×), dried ($Na_2SO_4$), and concentrated to dryness. Flash chromatography ion silica with 0-6% (2N $NH_3$-MeOH in $CH_2Cl_2$) afforded the product. M+1 552.

Biological Assays

The following assays were used to characterize the ability of compounds of the invention to inhibit the production of TNF-α and IL-1-β. The second assay can be used to measure the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a cyclooxygenase enzyme (COX-1 and COX-2) inhibition activity in vitro assay, can be used to characterize the ability of compounds of the invention to inhibit COX-1 and/or COX-2. The fifth assay, a Raf-kinase inhibition assay, can be used to characterize the compounds of the invention to inhibit phosphorylation of MEK by activated Raf-kinase.

Lipopolysaccharide-activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2×10^6$/mL in DMEM supplemented to contain 2% FCS, 10 mM, 0.3 mg/mL glutamate, 100 U/mL penicillin G and 100 mg/mL streptomycin sulfate (complete media). Cells were plated into Falcon flat bottom, 96 well culture plates (200 μL/well) and cultured overnight at 37° C. and 6% $CO_2$. Non-adherent cells were removed by washing with 200 μl/well of fresh medium. Wells containing adherent cells (~70% monocytes) were replenished with 100 μL of fresh medium.

Preparation of Test Compound Stock Solutions

Test compounds were dissolved in DMZ. Compound stock solutions were prepared to an initial concentration of 10-50 μM. Stocks were diluted initially to 20-200 μM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 μL complete medium. Monocytes were cultured with test compounds for 60 min at which time 25 μL of complete medium containing 30 ng/mL lipopolysaccharide from *E. coli* K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 μl/well of 3 μg/mL murine anti-human TNF-α MAb (R&D Systems #MAB210). Wells were then blocked for 1 h at room temperature with 200 ρL/well of $CaCl_2$-free ELISA buffer supplemented to contain 20 mg/mL BSA (standard ELISA buffer: 20 mM, 150 mM NaCl, 2 mM $CaCl_2$, 0.15 mM thimerosal, pH 7.4). Plates were washed and replenished with 100 μL of test supernatants (diluted 1:3) or standards. Standards consisted of eleven 1.5-fold serial dilutions from a stock of 1 ng/mL recombinant human TNF (R&D Systems). Plates were incubated at room temperature for 1 h on orbital shaker (300 rpm), washed and replenished with 100 μL/well of 0.5 μg/mL goat anti-human TNF-α (R&D systems #AB-210-NA) biotinylated at a 4:1 ratio. Plates were incubated for 40 min, washed and replenished with 100 μL/well of alkaline phosphatase-conjugated streptavidin (Jackson ImmunoResearch #016-050-084) at 0.02 μg/mL. Plates were incubated 30 min, washed and replenished with 200 μL/well of 1 mg/mL of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of EL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Lipopolysaccharide-activated THP1 Cell TNF Production Assay

THP1 cells are resuspended in fresh THP1 media (RPMI 1640, 10% heat-inactivated FBS, 1×PGS, 1×NEAA, plus 30 μM βME) at a concentration of 1E6/mL. One hundred microliters of cells per well are plated in a polystyrene 96-well tissue culture. One microgram per mL of bacterial LPS is prepared in THP1 media and is transferred to the wells. Test compounds are dissolved in 100% DMSO and are serially diluted 3 fold in a polypropylene 96-well microtiter plate (drug plate). HI control and LO control wells contain only DMSO. One microliter of test compound from the drug plate followed by 10 μL of LPS are transferred to the cell plate. The treated cells are induced to synthesize and secrete TNF-α at 37° C. for 3 h. Forty microliters of conditioned media are transferred to a 96-well polypropylene plate containing 110 μL of ECL buffer (50 mM Tris-HCl pH 8.0, 100 mM NaCl, 0.05% Tween 20, 0.05% NaN$_3$ and 1% FBS) supplemented with 0.44 nM MAB610 monoclonal Ab (R&D Systems), 0.34 nM ruthenylated AF210NA polyclonal Ab (R&D Systems) and 44 μg/mL sheep anti-mouse M280 Dynabeads (Dynal). After a 2 h incubation at room temperature with shaking, the reaction is read on the ECL M8 Instrument (IGEN Inc.). A low voltage is applied to the ruthenylated TNF-α immune complexes, which in the presence of TPA (the active component in Origlo), results in a cyclical redox reaction generating light at 620 nM. The amount of secreted TNF-α in the presence of compound compared with that in the presence of DMSO vehicle alone (HI control) is calculated using the formula: % control (POC)=(cpd−average LO)/(average HI−average LO)*100. Data (consisting of POC and inhibitor concentration in μM) is fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm.

Inhibition of LPS-Induced TNF-α Production in Mice

Male DBA/1LACJ mice are dosed with vehicle or test compounds in a vehicle (the vehicle consisting of 0.5% tragacanth in 0.03 N HCl) 30 minutes prior to lipopolysaccharide (2 mg/Kg, I.V.) injection. Ninety minutes after LPS injection, blood is collected and the serum is analyzed by ELISA for TNF-α levels.

Compounds of the invention may be shown to have anti-inflammatory properties in animal models of inflammation, including carageenan paw edema, collagen induced arthritis and adjuvant arthritis, such as the carageenan paw edema model (C. A. Winter et al Proc. Soc. Exp. Biol. Med. (1962) vol 111, p 544; K. F. Swingle, in R. A. Scherrer and M. W. Whitehouse, Eds., Anti-inflammatory Agents, Chemistry and Pharmacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/mL ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per mL DMSO and store aliquots at −20° C.; (d) 250 μM human glucagon (Peninsula): solubilize 0.5 mg vial in 575 μl 0.1N acetic acid (1 μL yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μL 10% BSA (heat-inactivated) and 990 μL Assay Buffer; (g) $^{125}$I-Glucagon (NEN, receptor-grade, 2200 Ci/mmol): dilute to 50,000 cpm/25 μL in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).
2. Add 10 mL Enzyme-free Dissoc. Fluid and hold for about 4 min at 37° C.
3. Gently tap cells free, triturate, take aliquot for counting and centrifuge remainder for 5 min at 1000 rpm.
4. Resuspend pellet in Assay Buffer at 75000 cells per 100 μL.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of I$^{125}$-glucagon binding in the presence of compounds of Formula I. The reagents are combined as follows:

|  | Compound/ Vehicle | 250 μM Glucagon | $^{125}$I- Glucagon | CHO/hGLUR Cells |
| --- | --- | --- | --- | --- |
| Total Binding + | —/5 μl | — | 25 μL | 100 μL |
| Compound | 5 μl/— | — | 25 μL | 100 μL |
| Nonspecific Binding | —/5 μl | 1 μl | 25 μL | 100 μL |

The mixture is incubated for 60 min at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10%FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 h on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2%FBS) and 1 ng human IL-1b/mL, and the cells incubated for 18-22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1N HCl, followed by neutralization with 1N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

Raf Kinase Assay

In vitro Raf kinase activity is measured by the extent of phosphorylation of the substrate MEK (Map kinase/ERK kinase) by activated Raf kinase, as described in GB 1,238,959 (incorporated herein by reference in its entirety). Phosphorylated MEK is trapped on a filter and incorporation of radiolabeled phosphate is quantified by scintillation counting.

Materials:
Activated Raf is produced by triple transfection of Sf9 cells with baculoviruses expressing "Glu-Glu"-epitope tagged Raf, $val^{12}$-H-Ras, and Lck. The "Glu-Glu"-epitope, Glu-Try-Met-Pro-Met-Glu, was fused to the carboxy-terminus of full length c-Raf.
Catalytically inactive MEK (K97A mutation) is produced in Sf9 cells transfected with a baculovirus expressing c-terminus "Glu-Glu" epitope-tagged K97A MEK1.
Anti "Glu-Glu" antibody was purified from cells grown as described in: Grussenmeyer, et al., Proceedings of the National Academy of Science, U.S.A. pp 7952-7954, 1985.
Column buffer: 20 mM Tris pH 8, 100 mM NaCl, 1 mM EDTA, 2.5 mM EGTA, 10 mM $MgCl_2$, 2 mM DTT, 0.4 mM AEBSF, 0.1% n-octylglucopyranoside, 1 nM okadeic acid, and 10 µg/mL each of benzamidine, leupeptin, pepstatin, and aprotinin.
5×Reaction buffer: 125 mM HEPES pH=8, 25 mM $MgCl_2$, 5 mM EDTA, 5 mM $Na_3VO_4$, 100 µg/mL BSA.
Enzyme dilution buffer: 25 mM HEPES pH 8, 1 mM EDTA, 1 mM $Na_3VO_4$, 400 µg/mL BSA.
Stop solution: 100 mM EDTA, 80 mM sodium pyrophosphate.
Filter plates: Milipore multiscreen #SE3MO78E3, Immobilon-P (PVDF).

Methods:
Protein purification: Sf9 cells were infected with baculovirus and grown as described in Williams, et al., Proceedings of the National Academy of Science, U.S.A. pp 2922-2926, 1992. All subsequent steps were preformed on ice or at 4° C. Cells were pelleted and lysed by sonication in column buffer. Lysates were spun at 17,000×g for 20 min, followed by 0.22 µm filtration. Epitope tagged proteins were purified by chromatography over GammaBind Plus affinity column to which the "Glu-Glu" antibody was coupled. Proteins were loaded on the column followed by sequential washes with two column volumes of column buffer, and eluted with 50 µg/mL Glu-Tyr-Met-Pro-Met-Glu in column buffer.
Raf kinase assay: Test compounds were evaluated using ten 3-fold serial dilutions starting at 10-100 µM. 10 µL of the test inhibitor or control, dissolved in 10% DMSO, was added to the assay plate followed by the addition of 30 µL of the a mixture containing 10 µL 5×reaction buffer, 1 mM $^{33}P$-γ-ATP (20 µCi/mL), 0.5 µL MEK (2.5 mg/mL), 1 µL 50 mM β-mercaptoethanol. The reaction was started by the addition of 10 µL of enzyme dilution buffer containing 1 mM DTT and an amount of activated Raf that produces linear kinetics over the reaction time course. The reaction was mixed and incubated at room temperature for 90 min and stopped by the addition of 50 µL stop solution. 90 µL aliquots of this stopped solution were transferred onto GFP-30 cellulose microtiter filter plates (Polyfiltronics), the filter plates washed in four well volumes of 5% phosphoric acid, allowed to dry, and then replenished with 25 µL scintillation cocktail. The plates were counted for $^{33}P$ gamma emission using a TopCount Scintillation Reader.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

For the treatment of TNF-α, IL-1β, IL-6, and IL-8 mediated diseases, cancer, and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating a TNF-α, IL-1, IL-6, and IL-8 mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

What is claimed is:

1. A compound of formula

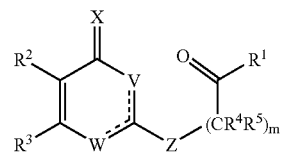

or a pharmaceutically acceptable salt thereof, wherein
V is —N(R$^8$)— or —N(R$^{16}$)— and W is —N═; or V is —N═ and W is —N(R$^8$)—;

X is O, S or $NR^9$;

Z is independently in each instance —O—, —N($R^9$)—, —N($R^{15}$)—, —S(=O)$_n$—, —C(=O)O—, —OC(=O)—, —C(=O)N($R^9$)—, —N($R^9$)C(=O)—, —S(=O)$_2$N($R^9$)—, —N($R^9$)S(=O)$_2$—, —C(=N$R^9$)N($R^9$)—, —OC(=O)N($R^9$)—, —N($R^9$)C(=O)O—, —N($R^9$)C(=O)N($R^9$)— or —N($R^9$)C(=N$R^9$)N($R^9$)—;

m in is 1, 2, 3, 4, 5 or 6;

n is independently in each instance 0, 1 or 2;

o is independently in each instance 0, 1, 2, 3 or 4;

$R^1$ is independently at each instance $C_{1-8}$alkyl substituted by 0 or 1 groups selected from $R^b$, —O(CH$_2$)$_o$$R^b$, —N($R^a$)(CH$_2$)$_o$$R^b$ and —S(=O)$_n$(CH$_2$)$_o$$R^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

$R^2$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of $R^{11}$, halo, cyano, —C(=O)R$^{11}$, —C(=O)OR$^{10}$, —C(=O)NR$^{12}$R$^{13}$, —C(NR$^{12}$)NR$^{12}$R$^{13}$, —OR$^{10}$, —O—C(=O)R$^{10}$, —O—C(=O)NR$^{12}$R$^{13}$, —O—C(=O)NR$^{14}$—S(=O)$_2$—R$^{11}$, —SR$^{10}$, —S(=O)R$^{11}$, —S(=O)$_2$—R$^{11}$, —S(=O)$_2$—NR$^{12}$R$^{13}$, —S(=O)$_2$—NR$^{14}$—C(=O)R$^{11}$, —S(=O)$_2$—NR$^{14}$—C(=O)OR$^{11}$, —S(=O)$_2$—NR$^{14}$—C(=O)NR$^{12}$R$^{13}$, —NR$^{12}$R$^{13}$, —NR$^{14}$—C(=O)R$^{10}$, —NR$^{14}$—C(=O)OR$^{11}$, —NR$^{14}$—C(=O)NR$^{12}$R$^{13}$, —NR$^{14}$—C(NR$^{12}$)NR$^{12}$R$^{13}$, —NR$^{14}$—S(=O)$_2$—R$^{11}$ or —NR$^{14}$S(=O)$_2$NR$^{12}$R$^{13}$;

$R^3$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of $R^{11}$, halo, cyano, —C(=O)R$^{11}$, —C(=O)OR$^{10}$, —C(=O)NR$^{12}$R$^{13}$, —C(NR$^{12}$)NR$^{12}$R$^{13}$, —OR$^{10}$, —O—C(=O)R$^{10}$, —O—C(=O)NR$^{12}$R$^{13}$, —O—C(=O)NR$^{14}$—S(=O)$_2$—R$^{11}$, —SR$^{10}$, —S(=O)R$^{11}$, —S(=O)$_2$—R$^{11}$, —S(=O)$_2$—NR$^{12}$R$^{13}$, —S(=O)$_2$—NR$^{14}$—C(=O)R$^{11}$, —S(=O)$_2$—NR$^{14}$—C(=O)OR$^{11}$, —S(=O)$_2$—NR$^{14}$—C(=O)NR$^{12}$R$^{13}$, —NR$^{12}$R$^{13}$, —NR$^{14}$—C(=O)R$^{10}$, —NR$^{14}$—C(=O)OR$^{11}$, —NR$^{14}$—C(=O)NR$^{12}$R$^{13}$, —NR$^{14}$—C(NR$^{12}$)NR$^{12}$R$^{13}$, —NR$^{14}$—S(=O)$_2$—R$^{11}$ or —NR$^{14}$—S(=O)$_2$—NR$^{12}$R$^{13}$;

provided that the total number of aryl, heteroaryl, cycloalkyl and heterocyclyl radicals substituted on each of $R^2$ and $R^3$ is 0 or 1;

$R^4$ and $R^5$ are each independently in each instance —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^a$)c(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl) —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, halo or cyano;

$R^6$ is independently in each instance hydrogen, —R$^1$ or -Z-R$^1$;

$R^7$ is independently in each instance hydrogen or —R$^1$;

$R^8$ is independently in each instance hydrogen or —R$^1$; provided that the total number of aryl, heteroaryl, cycloalkyl and heterocyclyl radicals in each —R$^1$ and -Z-R$^1$ is 0, 1, 2 or 3;

$R^9$ is independently at each instance hydrogen, $R^b$ or C$_{1-8}$alkyl substituted by 0 or 1 groups selected from $R^b$, —O(CH$_2$)$_o$$R^b$, —N(R$^a$)(CH$_2$)$_o$$R^b$ and —S(=O)$_n$(CH$_2$)$_o$ $R^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

$R^{10}$ is independently at each instance hydrogen or $R^{11}$;

$R^{11}$ is independently at each instance C$_{1-8}$alkyl substituted by 0 or 1 groups selected from $R^b$, —O(CH$_2$)$_o$$R^b$, —N(R$^a$)(CH$_2$)$_o$$R^b$ and S(=O)$_n$(CH$_2$)$_o$$R^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

$R^{12}$ is independently at each instance hydrogen, $R^b$ or C$_{1-8}$alkyl substituted by 0 or 1 groups selected from $R^b$, —O(CH$_2$)$_o$$R^b$, —N(R$^a$)(CH$_2$)$_o$$R^b$ and —S(=O)$_n$(CH$_2$)$_o$ $R^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

$R^{13}$ is independently at each instance: is independently at each instance hydrogen, $R^b$ or C$_{1-8}$alkyl substituted by 0 or 1 groups selected from $R^b$, —O(CH$_2$)$_o$$R^b$, —N(R$^a$)(CH$_2$)$_o$$R^b$ and S(=O)$_n$(CH$_2$)$_o$$R^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$ (C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{14}$ is independently at each instance hydrogen or C$_{1-8}$alkyl substituted by 0 or 1 groups selected from R$^b$, —O(CH$_2$)$_o$R$^b$, —N(R$^a$)(CH$_2$)$_o$R$^b$ and —S(=O)$_n$(CH$_2$)$_o$R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^8$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{15}$ and R$^{16}$ together represent a saturated or unsaturated 2-, 3- or 4-carbon bridge substituted by 0, 1 or 2 substituents selected from —OR$^a$, —N(R$^a$)R$^a$, —S(=O)$_n$(C$_{1-6}$alkyl), —C(=O)OR$^a$, —OC(=O)(C$_{1-6}$ alkyl), —C(=O)N(R$^a$)R$^a$, —N(R$^a$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$ (C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, halo and cyano;

R$^a$ is independently in each instance hydrogen or C$_{1-6}$alkyl; and

R$^b$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group; and wherein the phenyl, naphthyl or heterocycle is substituted with 0, 1, 2 or 3 substituents selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^a$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, cyano, halo, C$_{1-4}$alkyl and C$_{1-4}$haloalkyl.

2. The compound of claim 1 or a pharmaceutically acceptable salt thereof, wherein R$^3$ is a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of R$^{11}$, halo, cyano, —C(=O)R$^{11}$, —C(=O)OR$^{10}$, —C(=O)NR$^{12}$R$^{13}$, —C(NR$^{12}$)NR$^{12}$R$^{13}$, —OR$^{10}$, —O—C(=O)R$^{10}$, —O—C(=O)NR$^{12}$R$^{13}$, —O—C(=O)NR$^{14}$—S(=O)$_2$—R$^{11}$, —SR$^{10}$, —S(=O)R$^{11}$, —S(=O)$_2$—R$^{11}$, —S(=O)$_2$—NR$^{12}$R$^{13}$, —S(=O)$_2$—NR$^{14}$—C(=O)R$^{11}$, —S(=O)$_2$—NR$^{14}$—C(=O)OR$^{11}$, —S(=O)$_2$—NR$^{14}$—C(=O)NR$^{12}$R$^{13}$, —NR$^{12}$R$^{13}$, —NR$^{14}$—C(=O)R$^{10}$, —NR$^{14}$—C(=O)OR$^{11}$, —NR$^{14}$—C(=O)NR$^{12}$R$^{13}$, —NR$^{14}$—C(NR$^{12}$)NR$^{12}$R$^{13}$, —NR$^{14}$—S(=O)$_2$—R$^{11}$ or —NR$^{14}$—S(=O)$_2$—NR$^{12}$R$^{13}$.

3. The compound of claim 2 or a pharmaceutically acceptable salt thereof, wherein R$^3$ is pyridinyl or pyrimidinyl, either of which are substituted by 0, 1, 2 or 3 radicals of R$^{11}$, halo, cyano, —C(=O)R$^{11}$, —C(=O)OR$^{10}$, —C(=O)NR$^{12}$R$^{13}$, —C(NR$^{12}$)NR$^{12}$R$^{13}$, —OR$^{10}$, —O—C(=O)R$^{10}$, —O—C(=O)NR$^{12}$R$^{13}$, —O—C(=O)NR$^{14}$—S(=O)$_2$—R$^{11}$, —SR$^{10}$, —S(=O)R$^{11}$, —S(=O)$_2$—R$^{11}$, —S(=O)$_2$—NR$^{12}$R$^{13}$, —S(=O)$_2$—NR$^{14}$—C(=O)R$^{11}$, —S(=O)$_2$—NR$^{14}$—C(=O)OR$^{11}$, —S(=O)$_2$—NR$^{14}$—C(=O)NR$^{12}$R$^{13}$, —NR$^{12}$R$^{13}$, —NR$^{14}$—C(=O)R$^{10}$, —NR$^{14}$—C(=O)OR$^{11}$, —NR$^{14}$—C(=O)NR$^{12}$R$^{13}$, —NR$^{14}$—C(NR$^{12}$)NR$^{12}$R$^{13}$, —NR$^{14}$—S(=O)$_2$—R$^{11}$ or —NR$^{14}$—S(=O)$_2$—NR$^{12}$R$^{13}$.

4. The compound of claim 1 or a pharmaceutically acceptable salt thereof, wherein R$^2$ is phenyl or naphthyl, either of which is substituted by 0, 1, 2 or 3 radicals of R$^{11}$, halo, cyano, —C(=O)R$^{11}$, —C(=O)OR$^{10}$, —C(=O)NR$^{12}$R$^{13}$, —C(NR$^{12}$)NR$^{12}$R$^{13}$, —OR$^{10}$, —O—C(=O)R$^{10}$, —O—C(=O)NR$^{12}$R$^{13}$, —O—C(=O)NR$^{14}$—S(=O)$_2$R$^{11}$, —SR$^{10}$, —S(=O)R$^{11}$, —S(=O)$_2$—R$^{11}$, —S(=O)$_2$—NR$^{12}$R$^{13}$, —S(=O)$_2$—NR$^{14}$—C(=O)R$^{11}$, —S(=O)$_2$—NR$^{14}$—C(=O)OR$^{11}$, —S(=O)$_2$—NR$^{14}$—C(=O)NR$^{12}$R$^{13}$, —NR$^{12}$R$^{13}$, —NR$^{14}$—C(=O)R$^{10}$, —NR$^{14}$—C(=O)OR$^{11}$, —NR$^{14}$—C(=O)NR$^{12}$R$^{13}$, —NR$^{14}$—C(NR$^{12}$)NR$^{12}$R$^{13}$, —NR$^{14}$—S(=O)$_2$—R$^{11}$ or —NR$^{14}$S(=O)$_2$—NR$^{12}$R$^{13}$.

5. The compound of claim 1 or a pharmaceutically acceptable salt thereof, wherein R$^1$ is C$_{1-8}$alkyl.

6. The compound of claim 1 or a pharmaceutically acceptable salt thereof, wherein R$^1$ is independently at each instance C$_{1-8}$alkyl substituted by 0 or 1 groups selected from R$^b$, —O(CH$_2$)$_o$R$^b$, —N(R$^a$)(CH$_2$)$_o$R$^b$ and —S(=O)$_n$(CH$_2$)$_o$R$^b$; and additionally substituted by 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo.

7. The compound of claim 1 or a pharmaceutically acceptable salt thereof, wherein Z is —N(R$^9$)—, —N(R$^{15}$)—, —N(R$^9$)C(=O)—, —N(R$^9$)S(=O)$_2$—, —N(R$^9$)C(=O)O—, —N(R$^9$)C(=O)N(R$^9$)— or —N(R$^9$)C(=NR$^9$)N(R$^9$)—.

8. The compound of claim 1 or a pharmaceutically acceptable salt thereof, wherein R$^2$ is not pyridyl, pyrimidinyl, quinolyl or isoquinolinyl.

9. The compound of claim 1 or a pharmaceutically acceptable salt thereof, wherein V is —N(R$^8$)— or —N(R$^{16}$)— and W is —N=.

10. The compound of claim 1 or a pharmaceutically acceptable salt thereof, wherein V is —N= and W is —N(R$^8$)—.

11. A compound selected from:
2-[3-(4-Methoxy-phenyl)-2-oxo-propylamino]-3-methyl-5-naphthalen-2-yl-6-pyridin-4-yl-3H-pyrimidin-4-one;
2-[3-(4-Hydroxy-phenyl)-2-oxo-propylamino]-3-methyl-5-naphthalen-2-yl-6-pyridin-4-yl-3H-pyrimidin-4-one;
3-Methyl-5-naphthalen-2-yl-2-(2-oxo-3-phenyl-propylamino)-6-pyridin-4-yl-3H-pyrimidin-4-one;
2-(N'-Methoxy-N'-methylaminocarbonylmethylamino)-3-methyl-5-naphthalen-2-yl-6-pyridin-4-yl-3H-pyrimidin-4-one;
2-[3-(2-Methoxy-phenyl)-2-oxo-propylamino]-3-methyl-5-naphthalen-2-yl-6-pyridin-4-yl-3H-pyrimidin-4-one;

2-[3-(3-Methoxy-phenyl)-2-oxo-propylamino]-3-methyl-5-naphthalen-2-yl-6-pyridin-4-yl-3H-pyrimidin-4-one;
2-[3-Phenyl-2-oxo-propylamino]-3-methyl-5-naphthalen-2-yl-6-pyridin-4-yl-3H-pyrimidin-4-one;
2-[3-Phenyl-2-hydroxy-propylamino]-3-methyl-5-naphthalen-2-yl-6-pyridin-4-yl-3H-pyrimidin-4-one;
9-(2-Oxo-3-phenyl-propyl)-2-pyridin-4-yl-3-(3-trifluoromethyl-phenyl)-6,7,8,9-tetrahydro-pyrimido[1,2-a]pyrimidin-4-one;
9-(2-Oxo-4-phenyl-butyl)-2-pyridin-4-yl-3-(3-trifluoromethyl-phenyl)-6,7,8,9-tetrahydro-pyrimido[1,2-a]pyrimidin-4-one; and
9-(3-Cyclohexyl-2-oxo-propyl)-2-pyridin-4-yl-3-(3-trifluoromethyl-phenyl)-6,7,8,9-tetrahydro-pyrimido[1,2-a]pyrimidin-4-one; or a pharmaceutically acceptable salt thereof.

12. A pharmaceutical composition comprising a compound of Claim 1 and a pharmaceutically acceptable carrier or diluent.

13. A compound of formula

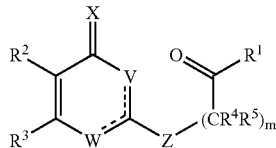

or a pharmaceutically acceptable salt thereof, wherein
V is —N($R^8$)— or —N($R^{16}$)— and W is —N=; or V is —N= and W is —N($R^8$)—;
X is O, S or N$R^9$;
Z is independently in each instance —O—, —N($R^9$)—, —N($R^{15}$)—, —S(=O)$_n$—, —C(=O)O—, —OC(=O)—, —C(=O)N($R^9$)—, —N($R^9$)C(=O)—, —S(=O)$_2$N($R^9$)—, —N($R^9$)S(=O)$_2$—, —C(=N$R^9$)N($R^9$)—, —OC(=O)N($R^9$)—, —N($R^9$)C(=O)O—, —N($R^9$)C(=O)N($R^9$)— or —N($R^9$)C(=N$R^9$)N($R^9$)—;
m is 1, 2, 3, 4, 5 or 6;
n is independently in each instance 0, 1 or 2;
o is independently in each instance 0, 1, 2, 3 or 4;
$R^1$ is independently at each instance $C_{1-8}$alkyl substituted by 0 or 1 groups selected from $R^b$, —O(CH$_2$)$_o$$R^b$, —N($R^a$)(CH$_2$)$_o$$R^b$ and —S(=O)$_n$(CH$_2$)$_o$$R^b$; and additionally substituted by 0, 1, 2 or 3 groups selected from —O$R^a$, —N($R^a$)$R^a$, —S(=O)$_n$(C$_{1-6}$alkyl), —C(=O)O$R^a$, —OC(=O)(C$_{1-6}$alkyl), —C(=O)N($R^a$)$R^a$, —N($R^9$)C(=O)(C$_{1-6}$alkyl), —S(=O)$_2$N($R^a$)$R^a$, —N($R^a$)S(=O)$_2$(C$_{1-6}$alkyl), —C(=N$R^a$)N($R^a$)$R^a$, —OC(=O)N($R^a$)$R^a$, —N($R^a$)C(=O)O$R^a$, —N($R^a$)C(=O)N($R^a$)$R^a$, —N($R^a$)C(=N$R^a$)N($R^a$)$R^a$, —OC(=O)N($R^a$)S(=O)$_2$(C$_{1-6}$alkyl), —S(=O)$_2$N($R^a$)C(=O)(C$_{1-6}$alkyl), —S(=O)$_2$N($R^a$)C(=O)O$R^a$, —S(=O)$_2$N($R^a$)C(=O)N($R^a$)$R^a$, —N($R^a$)S(=O)$_2$N($R^a$)$R^a$, oxo, cyano and halo;
$R^2$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of $R^{11}$, halo, cyano, —C(=O)$R^{11}$, —C(=O)O$R^{10}$, —C(=O)N$R^{12}$$R^{13}$, —C(N$R^{12}$)N$R^{12}$$R^{13}$, —O$R^{10}$, —O—C(=O)$R^{10}$, —O—C(=O)N$R^{12}$$R^{13}$, —O—C(=O)N$R^{14}$—S(=O)$_2$—$R^{11}$, —S$R^{10}$, —S(=O)$R^{11}$, —S(=O)$_2$—$R^{11}$, —S(=O)$_2$—N$R^{12}$$R^{13}$, —S(=O)$_2$—N$R^{14}$—C(=O)$R^{11}$, —S(=O)$_2$—N$R^{14}$—C(=O)O$R^{11}$, —S(=O)$_2$—N$R^{14}$—C(=O)N$R^{12}$$R^{13}$, —N$R^{12}$$R^{13}$, —N$R^{14}$—C(=O)$R^{10}$, —N$R^{14}$—C(=O)O$R^{11}$, —N$R^{14}$—C(=O)N$R^{12}$$R^{13}$, —N$R^{14}$—C(N$R^{12}$)N$R^{12}$$R^{13}$, —N$R^{14}$—S(=O)$_2$—$R^{11}$ or —N$R^{14}$S(=O)$_2$—N$R^{12}$$R^{13}$;

$R^3$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of $R^{11}$, halo, cyano, —C(=O)$R^{11}$, —C(=O)O$R^{10}$, —C(=O)N$R^{12}$$R^{13}$, —C(N$R^{12}$)N$R^{12}$$R^{13}$, —O$R^{10}$, —O—C(=O)$R^{10}$, —O—C(=O)N$R^{12}$$R^{13}$, —O—C(=O)N$R^{14}$—S(=O)$_2$—$R^{11}$, —S$R^{10}$, —S(=O)$R^{11}$, —S(=O)$_2$—$R^{11}$, —S(=O)$_2$—N$R^{12}$$R^{13}$, —S(=O)$_2$—N$R^{14}$—C(=O)$R^{11}$, —S(=O)$_2$—N$R^{14}$—C(=O)O$R^{11}$, —S(=O)$_2$—N$R^{14}$—C(=O)N$R^{12}$$R^{13}$, —N$R^{12}$$R^{13}$, —N$R^{14}$—C(=O)$R^{10}$, —N$R^{14}$—C(=O)O$R^{11}$, —N$R^{14}$—C(=O)N$R^{12}$$R^{13}$, —N$R^{14}$—C(N$R^{12}$)N$R^{12}$$R^{13}$, —N$R^{14}$—S(=O)$_2$—$R^{11}$ or —N$R^{14}$—S(=O)$_2$—N$R^{12}$$R^{13}$;

provided that the total number of aryl, heteroaryl, cycloalkyl and heterocyclyl radicals substituted on each of $R^2$ and $R^3$ is 0 or 1;

(CR$^4$R$^5$)$_m$ is $C_{1-6}$alkyl substituted by 1 or 2 substituents selected from —O$R^a$, —N($R^a$)$R^a$, —S(=O)$_n$(C$_{1-6}$alkyl), —C(=O)O$R^a$, —OC(=O)(C$_{1-6}$alkyl), —C(=O)N($R^a$)$R^a$, —N($R^a$)C(=O)(C$_{1-6}$alkyl), —S(=O)$_2$N($R^a$)$R^a$, —N($R^a$)S(=O)$_2$(C$_{1-6}$alkyl), —C(=N$R^a$)N($R^a$)$R^a$, —OC(=O)N($R^a$)$R^a$, —N($R^a$)C(=O)O$R^a$, —N($R^a$)C(=O)N($R^a$)$R^a$, —N($R^a$)C(N$R^a$)N($R^a$)$R^a$, —OC(=O)N($R^a$)S(=O)$_2$(C$_{1-6}$alkyl), —S(=O)$_2$N($R^a$)C(=O)(C$_{1-6}$alkyl), —S(=O)$_2$N($R^a$)C(=O)O$R^a$, —S(=O)$_2$N($R^a$)C(=O)N($R^a$)$R^a$, —N($R^a$)S(=O)$_2$N($R^a$)$R^a$, halo or cyano;

$R^6$ is independently in each instance hydrogen, —$R^1$ or -Z-$R^1$;
$R^7$ is independently in each instance hydrogen or —$R^1$;
$R^8$ is independently in each instance hydrogen or —$R^1$; provided that the total number of aryl, heteroaryl, cycloalkyl and heterocyclyl radicals in each —$R^1$ and -Z-$R^1$ is 0, 1, 2 or 3;
$R^9$ is independently at each instance hydrogen, $R^b$ or $C_{1-8}$alkyl substituted by 0 or 1 groups selected from $R^b$, —O(CH$_2$)$_o$$R^b$, —N($R^a$)(CH$_2$)$_o$$R^b$ and —S(=O)$_n$(CH$_2$)$_o$ $R^b$; and additionally substituted by 0, 1, 2 or 3 groups selected from —O$R^a$, —N($R^a$)$R^a$, —S(=O)$_n$(C$_{1-6}$alkyl), —C(=O)O$R^a$, —OC(=O)(C$_{1-6}$alkyl), —C(=O)N($R^a$)$R^a$, —N($R^9$)C(=O)(C$_{1-6}$alkyl), —S(=O)$_2$N($R^a$)$R^a$, —N($R^a$)S(=O)$_2$(C$_{1-6}$alkyl), —C(=N$R^a$)N($R^a$)$R^a$, —OC(=O)N($R^a$)$R^a$, —N($R^a$)C(=O)O$R^a$, —N($R^a$)C(=O)N($R^a$)$R^a$, —N($R^a$)C(=N$R^a$)N($R^a$)$R^a$, —OC(=O)N($R^a$)S(=O)$_2$(C$_{1-6}$alkyl), —S(=O)$_2$N($R^a$)C(=O)(C$_{1-6}$alkyl), —S(=O)$_2$N($R^a$)C(=O)O$R^a$, —S(=O)$_2$N($R^a$)C(=O)N($R^a$)$R^a$, —N($R^a$)S(=O)$_2$N($R^a$)$R^a$, oxo, cyano and halo;

$R^{10}$ is independently at each instance hydrogen or $R^{11}$;
$R^{11}$ is independently at each instance $C_{1-8}$alkyl substituted by 0 or 1 groups selected from $R^b$, —O(CH$_2$)$_o$$R^b$, —N($R^a$)(CH$_2$)$_o$$R^b$ and —S(=O)$_n$(CH$_2$)$_o$$R^b$; and additionally substituted by 0, 1, 2 or 3 groups selected from —O$R^a$, —N($R^a$)$R^a$, —S(=O)$_n$(C$_{1-6}$alkyl), —C(=O)O$R^a$, —OC(=O)(C$_{1-6}$alkyl), —C(=O)N($R^a$)$R^a$, —N($R^9$)C(=O)(C$_{1-6}$alkyl), —S(=O)$_2$N($R^a$)$R^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{12}$ is independently at each instance hydrogen, R$^b$ or C$_{1-8}$alkyl substituted by 0 or 1 groups selected from R$^b$, —O(CH$_2$)$_o$R$^b$, —N(R$^a$)(CH$_2$)$_o$R$^b$ and —S(=O)$_n$(CH$_2$)$_o$ R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{13}$ is independently at each instance: is independently at each instance hydrogen, R$^b$ or C$_{1-8}$alkyl substituted by 0 or 1 groups selected from R$^b$, —O(CH$_2$)$_o$R$^b$, —N(R$^a$)(CH$_2$)$_o$R$^b$ and S(=O)$_n$(CH$_2$)$_o$R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$ (C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{14}$ is independently at each instance hydrogen or C$_{1-8}$alkyl substituted by 0 or 1 groups selected from R$^b$, —O(CH$_2$)$_o$R$^b$, —N(R$^a$)(CH$_2$)$_o$R$^b$ and —S(=O)$_n$(CH$_2$)$_o$ R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{15}$ and R$^{16}$ together represent a saturated or unsaturated 2-, 3- or 4-carbon bridge substituted by 0, 1, 2 or 3 substituents selected from —OR$^a$, —N(R$^a$)R$^a$, —S(=O)$_n$(C$_{1-6}$alkyl), —C(=O)OR$^a$, —OC(=O)(C$_{1-6}$ alkyl), —C(=O)N(R$^a$)R$^a$, —N(R$^a$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$ (C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, halo and cyano;

R$^a$ is independently in each instance hydrogen or C$_{1-6}$alkyl; and

R$^b$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group; and wherein the phenyl, naphthyl or heterocycle is substituted with 0, 1, 2 or 3 substituents selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^a$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, cyano, halo, C$_{1-4}$alkyl and C$_{1-4}$haloalkyl.

14. A compound of formula

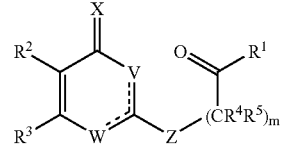

or a pharmaceutically acceptable salt thereof, wherein

V is —N(R$^8$)— or —N(R$^{16}$)— and W is —N=; or V is —N= and W is —N(R$^8$)—;

X is O, S or NR$^9$;

Z is independently in each instance —O—, —N(R$^9$)—, —N(R$^{15}$)—, —S(=O)$_n$—, —C(=O)O—, —OC(=O)—, —C(=O)N(R$^9$)—, —N(R$^9$)C(=O)—, —S(=O)$_2$N(R$^9$)—, —N(R$^9$)S(=o)$_2$—, —C(=NR$^9$)N(R$^9$)—, —OC(=O)N(R$^9$)—, —N(R$^9$)C(=O)O—, —N(R$^9$)C(=O)N(R$^9$)— or —N(R$^9$)C(NR$^9$)N(R$^9$)—;

m is 1, 2, 3, 4, 5 or 6;

n is independently in each instance 0, 1 or 2;

o is independently in each instance 0, 1, 2, 3 or 4;

R$^1$ is independently at each instance C$_{1-8}$alkyl substituted by 0 or 1 groups selected from R$^b$, —O(CH$_2$)$_o$R$^b$, —N(R$^a$)(CH$_2$)$_o$R$^b$ and —S(=O)$_n$(CH$_2$)$_o$R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^2$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of R$^{11}$, halo, cyano, —C(=O)R$^{11}$, —C(=O)OR$^{10}$, —C(=O)NR$^{12}$R$^{13}$, —C(NR$^{12}$)NR$^{12}$R$^{13}$, —OR$^{10}$, —O—C(=O)R$^{10}$, —O—C(=O)NR$^{12}$R$^{13}$, —O—C(=O)NR$^{14}$—S(=O)$_2$—R$^{11}$, —SR$^{10}$, —S(=O)R$^{11}$, —S(=O)$_2$—R$^{11}$, —S(=O)$_2$—NR$^{12}$R$^{13}$, —S(=O)$_2$—NR$^{14}$—C(=O)R$^{11}$, —S(=O)$_2$—NR$^{14}$—C(=O)OR$^{11}$, —S(=O)$_2$—NR$^{14}$—C(=O) NR$^{12}$R$^{13}$, —NR$^{12}$R$^{13}$, —NR$^{14}$—C(=O)R$^{10}$, —NR$^{14}$—C(=O)OR$^{11}$, —NR$^{14}$—C(=O)NR$^{12}$R$^{13}$, —NR$^{14}$—C(NR$^{12}$)NR$^{12}$R$^{13}$, —NR$^{14}$—S(=O)$_2$—R$^{11}$ or —NR$^{14}$S(=O)$_2$—NR$^{12}$R$^{13}$;

R$^3$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group, any of which are substituted by 0, 1, 2 or 3 radicals of R$^{11}$, halo, cyano, —C(=O)R$^{11}$, —C(=O)OR$^{10}$, —C(=O)NR$^{12}$R$^{13}$, —C(NR$^{12}$)NR$^{12}$R$^{13}$, —OR$^{10}$, —O—C(=O)R$^{10}$, —O—C(=O)NR$^{12}$R$^{13}$, —O—C(=O)NR$^{14}$—S(=O)$_2$—R$^{11}$, —SR$^{10}$, —S(=O)R$^{11}$, —S(=O)$_2$—R$^{11}$, —S(=O)$_2$—NR$^{12}$R$^{13}$, —S(=O)$_2$—NR$^{14}$—C(=O)R$^{11}$, —S(=O)$_2$—NR$^{14}$—C(=O)OR$^{11}$, —S(=O)$_2$—NR$^{14}$—C(=O)NR$^{12}$R$^{13}$, —NR$^{12}$R$^{13}$, —NR$^{14}$—C(=O)R$^{10}$, —NR$^{14}$—C(=O)OR$^{11}$, —NR$^{14}$—C(=O)NR$^{12}$R$^{13}$, —NR$^{14}$—C(NR$^{12}$)NR$^{12}$R$^{13}$, —NR$^{14}$—S(=O)$_2$—R$^{11}$ or —NR$^{14}$—S(=O)$_2$—NR$^{12}$R$^{13}$;

provided that the total number of aryl, heteroaryl, cycloalkyl and heterocyclyl radicals substituted on each of R$^2$ and R$^3$ is 0 or 1;

R$^4$ and R$^5$ are both H;

R$^6$ is independently in each instance hydrogen, —R$^1$ or -Z-R$^1$;

R$^7$ is independently in each instance hydrogen or —R$^1$;

R$^8$ is independently in each instance hydrogen or —R$^1$; provided that the total number of aryl, heteroaryl, cycloalkyl and heterocyclyl radicals in each —R$^1$ and -Z-R$^1$ is 0, 1, 2 or 3;

R$^9$ is independently at each instance hydrogen, R$^b$ or C$_{1-8}$alkyl substituted by 0 or 1 groups selected from R$^b$, —O(CH$_2$)$_o$R$^b$, —N(R$^a$)(CH$_2$)$_o$R$^b$ and —S(=O)$_n$(CH$_2$)$_o$ R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^a$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{10}$ is independently at each instance hydrogen or R$^{11}$;

R$^{11}$ is independently at each instance C$_{1-8}$alkyl substituted by 0 or 1 groups selected from R$^b$, —O(CH$_2$)$_o$R$^b$, —N(R$^a$)(CH$_2$)$_o$R$^b$ and —S(=O)$_n$(CH$_2$)$_o$R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{12}$ is independently at each instance hydrogen, R$^b$ or C$_{1-8}$alkyl substituted by 0 or 1 groups selected from R$^b$, —O(CH$_2$)$_o$R$^b$, —N(R$^a$)(CH$_2$)$_o$R$^b$ and S(=O)$_n$(CH$_2$)$_o$R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{13}$ is independently at each instance: is independently at each instance hydrogen, R$^b$ or C$_{1-8}$alkyl substituted by 0 or 1 groups selected from R$^b$, —O(CH$_2$)$_o$R$^b$, —N(R$^a$)(CH$_2$)$_o$R$^b$ and S(=O)$_n$(CH$_2$)$_o$R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{14}$ is independently at each instance hydrogen or C$_{1-8}$alkyl substituted by 0 or 1 groups selected from R$^b$, —O(CH$_2$)$_o$R$^b$, —N(R$^a$)(CH$_2$)$_o$R$^b$ and —S(=O)$_n$(CH$_2$)$_o$ R$^b$; and additionally substituted by 0, 1, 2 or 3 groups selected from —OR$^a$, —N(R$^a$)R$^a$, —S(=O)$_n$(C$_{1-6}$alkyl), —C(=O)OR$^a$, —OC(=O)(C$_{1-6}$alkyl), —C(=O)N(R$^a$)R$^a$, —N(R$^9$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$(C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, oxo, cyano and halo;

R$^{15}$ and R$^{16}$ together represent a saturated or unsaturated 2-, 3- or 4-carbon bridge substituted by 0, 1, 2 or 3 substituents selected from —OR$^a$, —N(R$^a$)R$^a$, —S(=O)$_n$(C$_{1-6}$alkyl), —C(=O)OR$^a$, —OC(=O)(C$_{1-6}$ alkyl), —C(=O)N(R$^a$)R$^a$, —N(R$^a$)C(=O)(C$_{1-6}$alkyl), —S(=O)$_2$N(R$^a$)R$^a$, —N(R$^a$)S(=O)$_2$(C$_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$ (C$_{1-6}$alkyl), —S(=O)$_2$N(R$^a$)C(=O)(C$_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, halo and cyano;

R$^a$ is independently in each instance hydrogen or C$_{1-6}$alkyl; and

R$^b$ is phenyl, naphthyl, or a saturated or unsaturated 5- or 6-membered ring heterocycle containing 1-4 heteroatoms selected from N, O and S, wherein no more than 2 of the heteroatoms are O or S, and the heterocycle is substituted by 0, 1 or 2 oxo groups and is optionally fused with a benzo group; and wherein the phenyl, naphthyl or heterocycle is substituted with 0, 1, 2 or 3 substituents selected from —OR$^a$, —N(R$^a$)R$^a$, —S(=O)$_n$ ($C_{1-6}$alkyl), —C(=O)OR$^a$, —OC(=O)($C_{1-6}$alkyl), —C(=O)N(R$^a$)R$^a$, —N(R$^a$)C(=O)($C_{1-6}$alkyl), —S(=O)$_2$N(R$^a$)R$^a$, —N(R$^a$)S(=O)$_2$($C_{1-6}$alkyl), —C(=NR$^a$)N(R$^a$)R$^a$, —OC(=O)N(R$^a$)R$^a$, —N(R$^a$)C(=O)OR$^a$, —N(R$^a$)C(=O)N(R$^a$)R$^a$, —N(R$^a$)C(=NR$^a$)N(R$^a$)R$^a$, —OC(=O)N(R$^a$)S(=O)$_2$($C_{1-6}$alkyl), —S(=O)$_2$N(R$^a$)C(=O)($C_{1-6}$alkyl), —S(=O)$_2$N(R$^a$)C(=O)OR$^a$, —S(=O)$_2$N(R$^a$)C(=O)N(R$^a$)R$^a$, —N(R$^a$)S(=O)$_2$N(R$^a$)R$^a$, cyano, halo, $C_{1-4}$alkyl and $C_{1-4}$haloalkyl.

15. A pharmaceutical composition comprising a compound of claim 14 and a pharmaceutically acceptable carrier or diluent.

* * * * *